United States Patent
Kawazoe

(10) Patent No.: US 8,440,838 B2
(45) Date of Patent: May 14, 2013

(54) ARYL (1H-1,2,4-TRIAZOL-1-YL) COMPOUND AND PROCESS FOR PRODUCTION THEREOF

(75) Inventor: Kentaro Kawazoe, Fuji (JP)

(73) Assignee: Ihara Chemical Industry Co., Ltd. (JP)

( * ) Notice: Subject to any disclaimer, the term of this patent is extended or adjusted under 35 U.S.C. 154(b) by 0 days.

(21) Appl. No.: 12/743,730

(22) PCT Filed: Nov. 28, 2008

(86) PCT No.: PCT/JP2008/003520
§ 371 (c)(1), (2), (4) Date: May 19, 2010

(87) PCT Pub. No.: WO2009/069312
PCT Pub. Date: Jun. 4, 2009

(65) Prior Publication Data
US 2010/0256386 A1    Oct. 7, 2010

(30) Foreign Application Priority Data
Nov. 30, 2007  (JP) ................. 2007-310537

(51) Int. Cl.
*C07D 249/14*     (2006.01)
(52) U.S. Cl.
USPC .................. 548/265.6; 548/269.4
(58) Field of Classification Search ........... 548/269.4
See application file for complete search history.

(56) References Cited

U.S. PATENT DOCUMENTS 4,925,864 A * 5/1990 Inamori et al. ............... 514/383
6,509,354 B1 * 1/2003 Toriyabe et al. ............. 514/317
7,872,036 B2 * 1/2011 Toriyabe et al. ............. 514/383
2009/0076282 A1 3/2009 Toriyabe et al.

FOREIGN PATENT DOCUMENTS

| JP | 2000-198768 | 7/2000 |
| JP | 2007-284356 | 11/2007 |
| WO | WO2006043635 | * 4/2006 |

* cited by examiner

*Primary Examiner* — Wu-Cheng Winston Shen
*Assistant Examiner* — Karen Cheng
(74) *Attorney, Agent, or Firm* — Bacon & Thomas, PLLC

(57) ABSTRACT

An aryl (1H-1,2,4-triazol-1-yl) compound is useful for producing a 3-(1H-1,2,4-triazol-1-yl)phenylsulfide compound (useful, e.g., as an insecticide). Also disclosed is a process for producing the compound. The aryl (1H-1,2,4-triazol-1-yl) compound is represented by the general formula (1), below, wherein R represents a C1-C6 alkyl group or a cyclic C3-C6 alkyl group; $A_1$ represents a hydrogen atom, an amino group, a mono(C1-C6 alkyl)amino group or a di(C1-C6 alkyl) amino group; $A_2$ represents a halogen atom, a C1-C6 alkyl group or a cyclic C3-C6 alkyl group; and Z represents a hydrogen atom, a halo-sulfonyl group or a mercapto group.

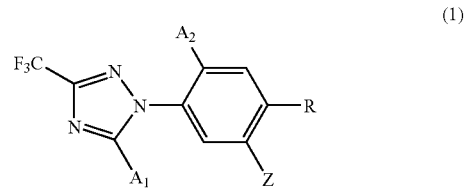

(1)

3 Claims, No Drawings

ARYL (1H-1,2,4-TRIAZOL-1-YL) COMPOUND AND PROCESS FOR PRODUCTION THEREOF

TECHNICAL FIELD

The present invention relates to an aryl (1H-1,2,4-triazol-1-yl) compound and a process for production of the compound.

BACKGROUND ART

A 3-(1H-1,2,4-triazol-1-yl)phenyl sulfide compound is known to be useful as an insecticide, miticide or nematicide (Patent Literature 1). In the Literature is described a method for production of 3-(1H-1,2,4-triazol-1-yl)phenyl sulfide compound, which comprises subjecting a precursor of the compound, i.e. a 3-(1H-1,2,4-triazol-1-yl)phenylmercaptan compound to alkylation.
Patent Literature 1: WO 2006/043635

DISCLOSURE OF THE INVENTION

Task to be Achieved by the Invention

Therefore, it has been desired to develop a 3-(1H-1,2,4-triazol-1-yl)phenylmercaptan compound useful for easy and efficient production of a 3-(1H-1,2,4-triazol-1-yl)phenyl sulfide compound useful as an insecticide, miticide or nematicide; a 3-(1H-1,2,4-triazol-1-yl)benzenesulfonyl halide compound which is an intermediate for production of the 3-(1H-1,2,4-triazol-1-yl)phenylmercaptan compound; a (1H-1,2,4-triazol-1-yl)benzene compound which is a precursor for the 3-(1H-1,2,4-triazol-1-yl)benzenesulfonyl halide compound; and processes for advantageously producing these compounds.

Means for Achieving the Task

In view of the above situation, the present inventor made a study on the 3-(1H-1,2,4-triazol-1-yl)phenylmercaptan compound, the 3-(1H-1,2,4-triazol-1-yl)benzenesulfonyl halide compound which is an intermediate for production of the 3-(1H-1,2,4-triazol-1-yl)phenylmercaptan compound, the (1H-1,2,4-triazol-1-yl)benzene compound which is a precursor for the 3-(1H-1,2,4-triazol-1-yl)benzenesulfonyl halide compound, and the processes for producing these compounds. As a result, it was found unexpectedly that the above task could be achieved by a series of steps comprised of reacting a triazole compound with a phenylboronic acid compound or a phenylboroxine compound in the presence of a catalytic amount of a copper compound, or reacting a triazole compound with a halobenzene compound having an electron withdrawing group at the 4-position, then converting the electron withdrawing group derived from raw compound into an alkyl group, and reacting the resulting compound with a halosulfonylating agent, and further reducing the resulting sulfonyl halide compound. The finding has led to the completion of the present invention.

Effect of the Invention

The present invention provides an aryl (1H-1,2,4-triazol-1-yl) compound and a process for producing the compound easily and efficiently. According to the present invention, an aryl (1H-1,2,4-triazol-1-yl) compound, which is useful for easy and efficient production of a 3-(1H-1,2,4-triazol-1-yl) phenyl sulfide compound useful as an insecticide, miticide or nematicide, can be produced by the above-mentioned series of steps, under mild conditions, at a high selectivity, efficiently and in an easy operation, without using any special reaction equipment.

BEST MODE FOR CARRYING OUT THE INVENTION

The present invention is described in detail below.
The present invention has achieved the above-mentioned task by providing the inventions shown in the following [1] to [25].

[1] An aryl (1H-1,2,4-triazol-1-yl) compound represented by the general formula (1)

[formula 1]

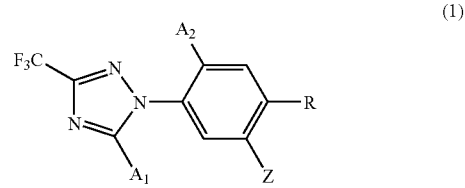

(1)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; $A_2$ is a halogen atom, a C1 to C6 alkyl group or a cyclic C3 to C6 alkyl group; and Z is a hydrogen atom, a halosulfonyl group or a mercapto group].

[2] An aryl (1H-1,2,4-triazol-1-yl) compound according to [1], wherein Z is a hydrogen atom.

[3] An aryl (1H-1,2,4-triazol-1-yl) compound according to [1], wherein Z is a halosulfonyl group.

[4] An aryl (1H-1,2,4-triazol-1-yl) compound according to [1], wherein Z is a mercapto group.

[5] A process for production of a (1H-1,2,4-triazol-1-yl)benzene compound represented the general formula (5)

[formula 5]

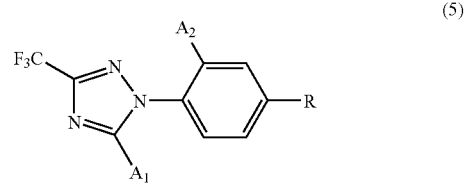

(5)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reacting a triazole compound represented by the general formula (2)

[formula 2]

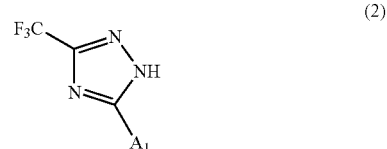

(2)

(wherein $A_1$ has the same definition as given above) with a phenylboronic acid compound represented by the general formula (3)

[formula 3]

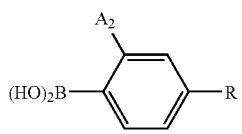

(3)

(wherein R and $A_2$ have the same definitions as given above) or a phenylboroxine compound represented by the general formula (4)

[formula 4]

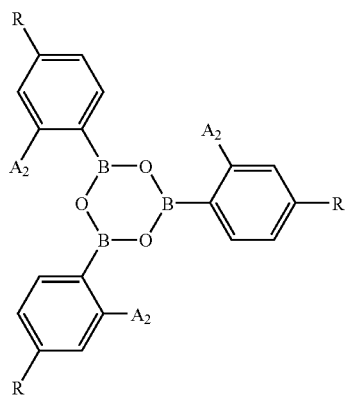

(4)

(wherein R and $A_2$ have the same definitions as given above) in the presence of a copper catalyst.

[6] A process for production of a (1H-1,2,4-triazol-1-yl)benzene compound represented the general formula (5)

[formula 8]

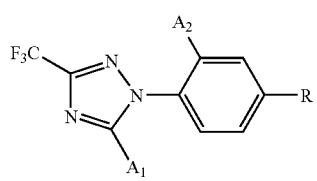

(5)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reacting a triazole compound represented by the general formula (2)

[formula 6]

(2)

(wherein $A_1$ has the same definition as give above) with a phenylboronic acid compound represented by the general formula (3)

[formula 7]

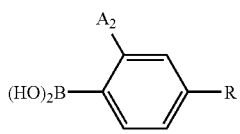

(3)

(wherein R and $A_2$ have the same definitions as given above) in the presence of a copper catalyst.

[7] A process for production of a (1H-1,2,4-triazol-1-yl)benzene compound represented by the general formula (5)

[formula 11]

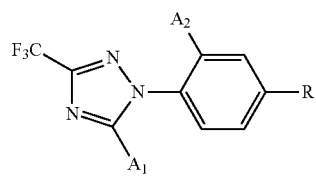

(5)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reacting a triazole compound represented by the general formula (2)

[formula 9]

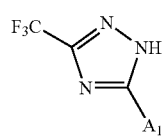

(2)

(wherein $A_1$ has the same definition as give above) with a phenylboroxine compound represented by the general formula (4)

[formula 10]

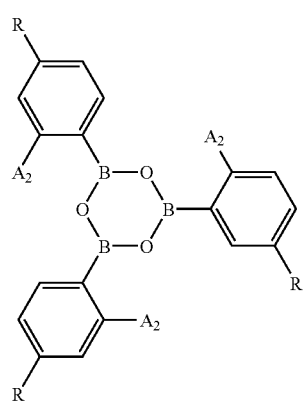

(4)

(wherein R and $A_2$ have the same definitions as given above) in the presence of a copper catalyst.

[8] A process for production of a (1H-1,2,4-triazol-1-yl)benzene compound, according to any of [5] to [7], wherein the copper catalyst is a copper compound having a 0 to 2 valency.

[9] A process for production of a (1H-1,2,4-triazol-1-yl)benzene compound, according to any of [5] to [8], wherein the copper catalyst is metallic copper or copper (II) acetate.

[10] A process for production of a (1H-1,2,4-triazol-1-yl)benzene compound, according to any of [5] to [9], wherein the reaction is conducted in the presence of a base.

[11] A process for production of a (1H-1,2,4-triazol-1-yl)benzene compound, according to [10], wherein the base is a tertiary amine compound.

[12] A process for production of a 4-substituted (1H-1,2,4-triazol-1-yl)benzene compound represented by the general formula (7)

[formula 14]

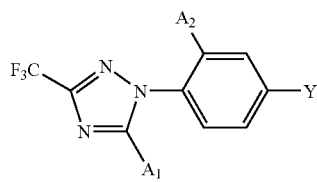

(7)

[wherein $A_1$ is a hydrogen atom, an amino group, a mono(C1 to C6 alkyl)amino group or a di(C1 to C6 alkyl)amino group; $A_2$ is a halogen atom, a C1 to C6 alkyl group or a cyclic C3 to C6 alkyl group; and Y is a cyano group, a formyl group, a carboxyl group or a metal salt thereof, or an alkxoycarbonyl group], which comprises reacting a 4-substituted-halobenzene compound represented by the general formula (6)

[formula 12]

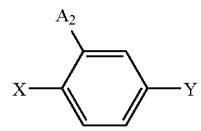

(6)

(wherein $A_2$ and Y have the same definitions as given above, and X is a halogen atom) with a triazole compound represented by the general formula (2)

[formula 13]

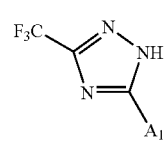

(2)

(wherein $A_1$ has the same definition as given above) in the presence of a base.

[13] A process for production of a 4-substituted (1H-1,2,4-triazol-1-yl)benzene compound, according to [12], wherein Y is a cyano group.

[14] A process for production of a 4-(1H-1,2,4-triazol-1-yl) toluene compound represented by the general formula (8)

[formula 16]

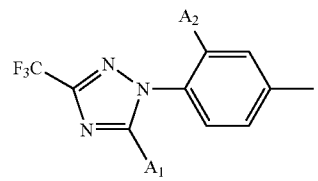

(8)

[wherein $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reducing the substituent group Y of a 4-substituted (1H-1,2,4-triazol-1-yl)benzene compound represented by the general formula (7)

[formula 15]

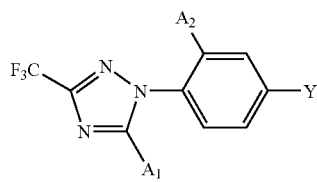

(7)

(wherein $A_1$ and $A_2$ have the same definitions as given above; and Y is a cyano group, a formyl group, a carboxyl group or a metal salt thereof, or an alkxoycarbonyl group).

[15] A process for production of a 4-(1H-1,2,4-triazol-1-yl) toluene compound, according to [14], wherein Y is a cyano group.

[16] A process for production of a 4-(1H-1,2,4-triazol-1-yl) toluene compound, according to [14] or [15], wherein the reduction is conducted in the presence of a reducing agent and a heterogeneous metal catalyst.

[17] A process for production of a 4-(1H-1,2,4-triazol-1-yl) toluene compound, according to any of [14] to [16], wherein the heterogeneous metal catalyst is palladium carbon.

[18] A process for production of a 4-(1H-1,2,4-triazol-1-yl) toluene compound, according to any of [14] to [17], wherein the reducing agent is ammonium formate.

[19] A process for production of a 4-(1H-1,2,4-triazol-1-yl) toluene compound represented by the general formula (8)

[formula 19]

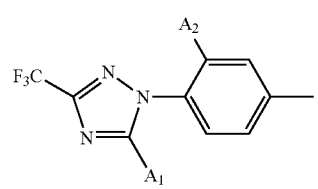

(8)

[wherein $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reacting a 4-cyano-1-(1H-1,2,4-triazol-1-yl)benzene compound represented by the general formula (7')

[formula 17]

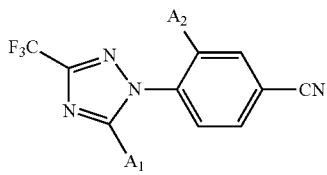

(7')

(wherein $A_1$ and $A_2$ have the same definitions as given above) in ethanol in the presence of a Raney nickel catalyst to convert the compound into a diethylamine compound represented by the general formula (9)

[formula 18]

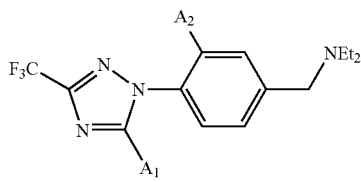

(9)

(wherein $A_1$ and $A_2$ have the same definitions as give above) and then reducing the compound of general formula (9) in the presence of a reducing agent and a heterogeneous metal catalyst.

[20] A process for production of a 4-(1H-1,2,4-triazol-1-yl) toluene compound, according to [19], wherein the heterogeneous metal catalyst is palladium (II) hydroxide carbon.

[21] A process for production of a 4-(1H-1,2,4-triazol-1-yl) toluene compound, according to [19] or [20], wherein the reducing agent is hydrogen.

[22] A process for production of a 3-(1H-1,2,4-triazol-1-yl) benzenesulfonyl halide compound represented by the general formula (10)

[formula 21]

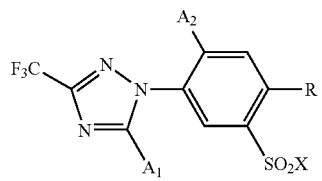

(10)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; $A_2$ is a halogen atom, a C1 to C6 alkyl group or a cyclic C3 to C6 alkyl group; and X is a halogen atom], which comprises reacting a (1H-1,2,4-triazol-1-yl)benzene compound represented by the general formula (5)

[formula 20]

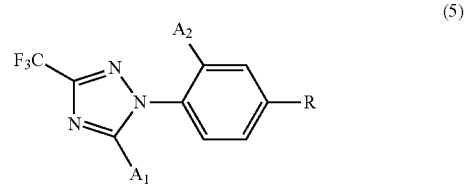

(5)

(wherein R, $A_1$ and $A_2$ have the same definitions as given above) with a halosulfonylating agent.

[23] A process for production of a 3-(1H-1,2,4-triazol-1-yl) benzenesulfonyl halide compound, according to [22], wherein the halosulfonylating agent is chlorosulfonic acid.

[24] A process for production of a 3-(1H-1,2,4-triazol-1-yl) phenyl mercaptan compound represented by the general formula (11)

[formula 23]

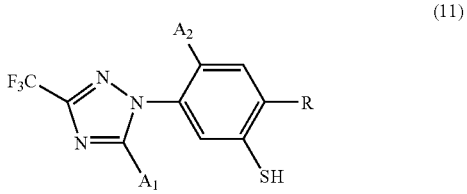

(11)

[wherein R is a C1 to C6 alkyl group or a cyclic C3 to C6 alkyl group; $A_1$ is a hydrogen atom, an amino group, a mono(C1 to C6 alkyl)amino group or a di(C1 to C6 alkyl)amino group; and $A_2$ is a halogen atom, a C1 to C6 alkyl group or a cyclic C3 to C6 alkyl group], which comprises reducing a 3-(1H-1,2,4-triazol-1-yl)benzenesulfonyl halide compound represented by the general formula (10)

[formula 22]

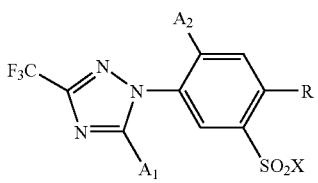

(10)

(wherein R, $A_1$ and $A_2$ have the same definitions as given above, and X is a halogen atom).

[25] A process for production of a 3-(1H-1,2,4-triazol-1-yl) phenyl mercaptan compound, according to [24], wherein the reaction is conducted in the presence of an acid.

The present invention is described in detail below.

The present invention provides an aryl (1H-1,2,4-triazol-1-yl) compound represented by the general formula (1) and a process for production of the compound, an intermediate for producing the compound, and a precursor thereof.

Description is made first on the aryl (1H-1,2,4-triazol-1-yl) compound represented by the general formula (1).

In the general formula (1), R is a straight chain or branched chain alkyl group having 1 to 6 carbon atoms (hereinafter, the carbon atoms are abbreviated as "C1 to C6" in this case), such as methyl group, ethyl group, n-propyl group, isopropyl group, n-butyl group, sec-butyl group, tert-butyl group, n-pentyl group, n-hexyl group or the like, or a cyclic C3 to C6 alkyl group such as cyclopropyl group, cyclobutyl group, cyclopentyl group, cyclohexyl group or the like; $A_1$ is a hydrogen atom, an amino group, a straight chain or branched chain C1 to C6 alkylamino group, such as methylamino group, ethylamino group or the like, or a straight chain or branched chain di(C1 to C6 alkyl)amino group such as dimethylamino group or the like; $A_2$ is a halogen atom such as fluorine atom, chlorine atom, bromine atom, iodine atom or the like, a straight chain or branched C1 to C6 alkyl group such as methyl group, ethyl group, n-propyl group, isopropyl group, n-butyl group, sec-butyl group, tert-butyl group, n-pentyl group, n-hexyl group or the like, or a cyclic C3 to C6 alkyl group such as cyclopropyl group, cyclobutyl group, cyclopentyl group, cyclohexyl group or the like; and Z is a hydrogen atom, a halosulfonyl group such as chlorosulfonyl group, fluorosulfonyl group, bromosulfonyl group or the like, or a mercapto group.

As specific examples of the aryl (1H-1,2,4-triazol-1-yl) compound represented by the general formula (1), there can be mentioned; 3-fluoro-4-(3-trifluoromethyl-1H-1,2,4-triazol-1-yl)toluene, 4-fluoro-2-methyl-5-(3-trifluoromethyl-1H-1,2,4-triazol-1-yl)benzenesulfonyl chloride, 4-fluoro-2-methyl-5-(3-trifluoromethyl-1H-1,2,4-triazol-1-yl) benzenesulfonyl fluoride, 4-fluoro-2-methyl-5-(3-trifluoromethyl-1H-1,2,4-triazol-1-yl)thiophenol, 3-chloro-4-(3-trifluoromethyl-1H-1,2,4-triazol-1-yl)toluene, 4-chloro-2-methyl-5-(3-trifluoromethyl-1H-1,2,4-triazol-1-yl)benzenesulfonyl chloride, 4-chloro-2-methyl-5-(3-trifluoromethyl-1H-1,2,4-triazol-1-yl)benzenesulfonyl fluoride, 4-chloro-2-methyl-5-(3-trifluoromethyl-1H-1,2,4-triazol-1-yl)thiophenol, 2,4-dimethyl-1-(3-trifluoromethyl-1H-1,2,4-triazol-1-yl)benzene, 2,4-dimethyl-5-(3-trifluoromethyl-1H-1,2,4-triazol-1-yl)benzenesulfonyl chloride, 2,4-dimethyl-5-(3-trifluoromethyl-1H-1,2,4-triazol-1-yl)benzenesulfonyl fluoride, 2,4-dimethyl-5-(3-trifluoromethyl-1H-1,2,4-triazol-1-yl)thiophenol, 3-ethyl-4-(3-trifluoromethyl-1H-1,2,4-triazol-1-yl)toluene, 4-ethyl-2-methyl-5-(3-trifluoromethyl-1H-1,2,4-triazol-1-yl)benzenesulfonyl chloride, 4-ethyl-2-methyl-5-(3-trifluoromethyl-1H-1,2,4-triazol-1-yl) benzenesulfonyl fluoride, 4-ethyl-2-methyl-5-(3-trifluoromethyl-1H-1,2,4-triazol-1-yl)thiophenol, 3-isopropyl-4-(3-trifluoromethyl-1H-1,2,4-triazol-1-yl)toluene, 4-isopropyl-2-methyl-5-(3-trifluoromethyl-1H-1,2,4-triazol-1-yl)benzenesulfonyl chloride, 4-isopropyl-2-methyl-5-(3-trifluoromethyl-1H-1,2,4-triazol-1-yl) benzenesulfonyl fluoride, 4-isopropyl-2-methyl-5-(3-trifluoromethyl-1H-1,2,4-triazol-1-yl)thiophenol, 3-cyclopropyl-4-(3-trifluoromethyl-1H-1,2,4-triazol-1-yl)toluene, 4-cyclopropyl-2-methyl-5-(3-trifluoromethyl-1H-1,2,4-triazol-1-yl)benzenesulfonyl chloride, 4-cyclopropyl-2-methyl-5-(3-trifluoromethyl-1H-1,2,4-triazol-1-yl) benzenesulfonyl fluoride, 4-cyclopropyl-2-methyl-5-(3-trifluoromethyl-1H-1,2,4-triazol-1-yl)thiophenol, 4-(5-amino-3-trifluoromethyl-1H-1,2,4-triazol-1-yl)-3-fluorotoluene, 5-(5-amino-3-trifluoromethyl-1H-1,2,4-triazol-1-yl)-4-fluoro-2-methylbenzenesulfonyl chloride, 5-(5-amino-3-trifluoromethyl-1H-1,2,4-triazol-1-yl)-4-fluoro-2-methylbenzenesulfonyl fluoride, 5-(5-amino-3-trifluoromethyl-1H-1,2,4-triazol-1-yl)-4-fluoro-2-methylthiophenol, 4-(5-amino-3-trifluoromethyl-1H-1,2,4-triazol-1-yl)-3-chlorotoluene, 5-(5-amino-3-trifluoromethyl-1H-1,2,4-triazol-1-yl)-4-chloro-2-methylbenzenesulfonyl chloride, 5-(5-amino-3-trifluoromethyl-1H-1,2,4-triazol-1-yl)-4-chloro-2-methylbenzenesulfonyl fluoride, 5-(5-amino-3-trifluoromethyl-1H-1,2,4-triazol-1-yl)-4-chloro-2-methylthiophenol, 1-(5-amino-3-trifluoromethyl-1H-1,2,4-triazol-1-yl)-2,4-dimethylbenzene, 5-(5-amino-3-trifluoromethyl-1H-1,2,4-triazol-1-yl)-2,4-dimethylbenzenesulfonyl chloride, 5-(5-amino-3-trifluoromethyl-1H-1,2,4-triazol-1-yl)-2,4-dimethylbenzenesulfonyl fluoride, 5-(5-amino-3-trifluoromethyl-1H-1,2,4-triazol-1-yl)-2,4-dimethylthiophenol, 4-(5-amino-3-trifluoromethyl-1H-1,2,4-triazol-1-yl)-3-ethyltoluene, 5-(5-amino-3-trifluoromethyl-1H-1,2,4-triazol-1-yl)-4-ethyl-2-methylbenzenesulfonyl chloride, 5-(5-amino-3-trifluoromethyl-1H-1,2,4-triazol-1-yl)-4-ethyl-2-methylbenzenesulfonyl fluoride, 5-(5-amino-3-trifluoromethyl-1H-1,2,4-triazol-1-yl)-4-ethyl-2-methylthiophenol, 4-(5-amino-3-trifluoromethyl-1H-1,2,4-triazol-1-yl)-3-isopropyltoluene, 5-(5-amino-3-trifluoromethyl-1H-1,2,4-triazol-1-yl)-4-isopropyl-2-methylbenzenesulfonyl chloride, 5-(5-amino-3-trifluoromethyl-1H-1,2,4-triazol-1-yl)-4-isopropyl-2-methylbenzenesulfonyl fluoride, 5-(5-amino-3-trifluoromethyl-1H-1,2,4-triazol-1-yl)-4-isopropyl-2-methylthiophenol, 4-(5-amino-3-trifluoromethyl-1H-1,2,4-triazol-1-yl)-3-cyclopropyltoluene, 5-(5-amino-3-trifluoromethyl-1H-1,2,4-triazol-1-yl)-4-cyclopropyl-2-methylbenzenesulfonyl chloride, 5-(5-amino-3-trifluoromethyl-1H-1,2,4-triazol-1-yl)-4-cyclopropyl-2-methylbenzenesulfonyl fluoride, 5-(5-amino-3-trifluoromethyl-1H-1,2,4-triazol-1-yl)-4-cyclopropyl-2-methylthiophenol, 3-fluoro-4-(5-methylamino-3-trifluoromethyl-1H-1,2,4-triazol-1-yl)toluene, 4-fluoro-2-methyl-5-(5-methylamino-3-trifluoromethyl-1H-1,2,4-triazol-1-yl)benzenesulfonyl chloride, 4-fluoro-2-methyl-5-(5-methylamino-3-trifluoromethyl-1H-1,2,4-triazol-1-yl) benzenesulfonyl fluoride, 4-fluoro-2-methyl-5-(5-methylamino-3-trifluoromethyl-1H-1,2,4-triazol-1-yl) thiophenol, 3-chloro-4-(5-methylamino-3-trifluoromethyl-1H-1,2,4-triazol-1-yl)toluene, 4-chloro-2-methyl-5-(5-methylamino-3-trifluoromethyl-1H-1,2,4-triazol-1-yl) benzenesulfonyl chloride, 4-chloro-2-methyl-5-(5-methylamino-3-trifluoromethyl-1H-1,2,4-triazol-1-yl) benzenesulfonyl fluoride, 4-chloro-2-methyl-5-(5-methylamino-3-trifluoromethyl-1H-1,2,4-triazol-1-yl) thiophenol, 2,4-dimethyl-1-(5-methylamino-3-trifluoromethyl-1H-1,2,4-triazol-1-yl)benzene, 2,4-dimethyl-5-(5-methylamino-3-trifluoromethyl-1H-1,2,4-triazol-1-yl)benzenesulfonyl chloride, 2,4-dimethyl-5-(5-methylamino-3-trifluoromethyl-1H-1,2,4-triazol-1-yl) benzenesulfonyl fluoride, 2,4-dimethyl-5-(5-methylamino-3-trifluoromethyl-1H-1,2,4-triazol-1-yl)thiophenol, 3-ethyl-4-(5-methylamino-3-trifluoromethyl-1H-1,2,4-triazol-1-yl) toluene, 4-ethyl-2-methyl-5-(5-methylamino-3-trifluoromethyl-1H-1,2,4-triazol-1-yl)benzenesulfonyl chloride, 4-ethyl-2-methyl-5-(5-methylamino-3-trifluoromethyl-1H-1,2,4-triazol-1-yl)benzenesulfonyl fluoride, 4-ethyl-2-methyl-5-(5-methylamino-3-trifluoromethyl-1H-1,2,4-triazol-1-yl)thiophenol, 3-isopropyl-4-(5-methylamino-3-trifluoromethyl-1H-1,2,4-triazol-1-yl)toluene, 4-isopropyl-2-methyl-5-(5-methylamino-3-trifluoromethyl-1H-1,2,4-triazol-1-yl)benzenesulfonyl chloride, 4-isopropyl-2-methyl-5-(5-methylamino-3-trifluoromethyl-1H-1,2,4-triazol-1-yl)benzenesulfonyl fluoride, 4-isopropyl-2-methyl-5-(5-methylamino-3-trifluoromethyl-1H-1,2,4-triazol-1-yl)thiophenol, 3-cyclopropyl-4-(5-methylamino-3-trifluoromethyl-1H-1,2,4-triazol-1-yl)toluene, 4-cyclopropyl-2-methyl-5-(5-methylamino-3-trifluoromethyl-1H-1,2,4-triazol-1-yl)benzenesulfonyl chloride, 4-cyclopropyl-2-methyl-5-(5-methylamino-3-trifluoromethyl-1H-1,2,4-triazol-1-yl)benzenesulfonyl fluoride, 4-cyclopropyl-2-methyl-5-(5-methylamino-3-trifluoromethyl-1H-1,2,4-triazol-1-yl)thiophenol, 4-(5-dimethylamino-3-trifluoromethyl-1H-1,2,4-triazol-1-yl)-3-fluorotoluene, 5-(5-dimethylamino-3-trifluoromethyl-1H-1,2,4-triazol-1-yl)-4-fluoro-2-methylbenzenesulfonyl chloride, 5-(5-dimethylamino-3-trifluoromethyl-1H-1,2,4-triazol-1-yl)-4-fluoro-2-methylbenzenesulfonyl fluoride, 5-(5-dimethylamino-3-trifluoromethyl-1H-1,2,4-triazol-1-yl)-4-fluoro-2-methylthiophenol, 3-chloro-4-(5-dimethylamino-3-trifluoromethyl-1H-1,2,4-triazol-1-yl)toluene, 4-chloro-5-(5-dimethylamino-3-trifluoromethyl-1H,1,2,4-triazol-1-yl)-2-methylbenzenesulfonyl chloride, 4-chloro-5-(5-dimethylamino-3-trifluoromethyl-1H-1,2,4-triazol-1-yl)-2-methylbenzenesulfonyl fluoride, 4-chloro-5-(5-dimethylamino-3-trifluoromethyl-1H,1,2,4-triazol-1-yl)-2-methylthiophenol, 1-(5-dimethylamino-3-trifluoromethyl-1H-1,2,4-triazol-1-yl)-2,4-dimethylbenzene, 5-(5-dimethylamino-3-trifluoromethyl-1H-1,2,4-triazol-1-yl)-2,4-dimethylbenzenesulfonyl chloride, 5-(5-dimethylamino-3-trifluoromethyl-1H-1,2,4-triazol-1-yl)-2,4-dimethylbenzenesulfonyl fluoride, 5-(5-dimethylamino-3-trifluoromethyl-1H-1,2,4-triazol-1-yl)-2,4-dimethylthiophenol, 3-ethyl-4-(5-dimethylamino-3-trifluoromethyl-1H-1,2,4-triazol-1-yl)toluene, 4-ethyl-5-(5-dimethylamino-3-trifluoromethyl-1H-1,2,4-triazol-1-yl)-2-methylbenzenesulfonyl chloride, 4-ethyl-5-(5-dimethylamino-3-trifluoromethyl-1H-1,2,4-triazol-1-yl)-2-methylbenzenesulfonyl fluoride, 4-ethyl-5-(5-dimethylamino-3-trifluoromethyl-1H-1,2,4-triazol-1-yl)-2-methylthiophenol, 4-(5-dimethylamino-3-trifluoromethyl-1H-1,2,4-triazol-1-yl)-3-isopropyltoluene, 5-(5-dimethylamino-3-trifluoromethyl-1H-1,2,4-triazol-1-yl)-4-isopropyl-2-methylbenzenesulfonyl chloride, 5-(5-dimethylamino-3-trifluoromethyl-1H-1,2,4-triazol-1-yl)-4-isopropyl-2-methylbenzenesulfonyl fluoride, 5-(5-dimethylamino-3-trifluoromethyl-1H-1,2,4-triazol-1-yl)-4-isopropyl-2-methylthiophenol, 3-cyclopropyl-4-(5-dimethylamino-3-trifluoromethyl-1H-1,2,4-triazol-1-yl)toluene, 4-cyclopropyl-5-(5-dimethylamino-3-trifluoromethyl-1H-1,2,4-triazol-1-yl)-2-methylbenzenesulfonyl chloride, 4-cyclopropyl-5-(5-dimethylamino-3-trifluoromethyl-1H-1,2,4-triazol-1-yl)-2-methylbenzenesulfonyl fluoride, 4-cyclopropyl-5-(5-dimethylamino-3-trifluoromethyl-1H-1,2,4-triazol-1-yl)-2-methylthiophenol, 3-fluoro-4-(3-trifluoromethyl-1H-1,2,4-triazol-1-yl)-1-ethylbenzene, 2-ethyl-4-fluoro-5-(3-trifluoromethyl-1H-1,2,4-triazol-1-yl)benzenesulfonyl chloride, 2-ethyl-4-fluoro-5-(3-trifluoromethyl-1H-1,2,4-triazol-1-yl)benzenesulfonyl fluoride, 2-ethyl-4-fluoro-5-(3-trifluoromethyl-1H-1,2,4-triazol-1-yl)thiophenol, 3-chloro-4-(3-trifluoromethyl-1H-1,2,4-triazol-1-yl)-1-ethylbenzene, 4-chloro-2-ethyl-5-(3-trifluoromethyl-1H-1,2,4-triazol-1-yl)benzenesulfonyl chloride, 4-chloro-2-ethyl-5-(3-trifluoromethyl-1H-1,2,4-triazol-1-yl)benzenesulfonyl fluoride, 4-chloro-2-ethyl-5-(3-trifluoromethyl-1H-1,2,4-triazol-1-yl)thiophenol, 5-ethyl-2-(3-trifluoromethyl-1H-1,2,4-triazol-1-yl)toluene, 2-ethyl-4-methyl-5-(3-trifluoromethyl-1H-1,2,4-triazol-1-yl)benzenesulfonyl chloride, 2-ethyl-4-methyl-5-(3-trifluoromethyl-1H-1,2,4-triazol-1-yl)benzenesulfonyl fluoride, 2-ethyl-4-methyl-5-(3-trifluoromethyl-1H-1,2,4-triazol-1-yl)thiophenol, 2,4-diethyl-1-(3-trifluoromethyl-1H-1,2,4-triazol-1-yl)benzene, 2,4-diethyl-5-(3-trifluoromethyl-1H-1,2,4-triazol-1-yl)benzenesulfonyl chloride, 2,4-diethyl-5-(3-trifluoromethyl-1H-1,2,4-triazol-1-yl)benzenesulfonyl fluoride, 2,4-diethyl-5-(3-trifluoromethyl-1H-1,2,4-triazol-1-yl)thiophenol, 3-isopropyl-4-(3-trifluoromethyl-1H-1,2,4-triazol-1-yl)-1-ethylbenzene, 2-ethyl-4-isopropyl-5-(3-trifluoromethyl-1H-1,2,4-triazol-1-yl)benzenesulfonyl chloride, 2-ethyl-4-isopropyl-5-(3-trifluoromethyl-1H-1,2,4-triazol-1-yl)benzenesulfonyl fluoride, 2-ethyl-4-isopropyl-5-(3-trifluoromethyl-1H-1,2,4-triazol-1-yl)thiophenol, 3-cyclopropyl-4-(3-trifluoromethyl-1H-1,2,4-triazol-1-yl)-1-ethylbenzene, 4-cyclopropyl-2-ethyl-5-(3-trifluoromethyl-1H-1,2,4-triazol-1-yl)benzenesulfonyl chloride, 4-cyclopropyl-2-ethyl-5-(3-trifluoromethyl-1H-1,2,4-triazol-1-yl)benzenesulfonyl fluoride, 4-cyclopropyl-2-ethyl-5-(3-trifluoromethyl-1H-1,2,4-triazol-1-yl)thiophenol, 4-(5-amino-3-trifluoromethyl-1H-1,2,4-triazol-1-yl)-3-fluoro-1-ethylbenzene, 5-(5-amino-3-trifluoromethyl-1H-1,2,4-triazol-1-yl)-2-ethyl-4-fluorobenzenesulfonyl chloride, 5-(5-amino-3-trifluoromethyl-1H-1,2,4-triazol-1-yl)-2-ethyl-4-fluorobenzenesulfonyl fluoride, 5-(5-amino-3-trifluoromethyl-1H-1,2,4-triazol-1-yl)-2-ethyl-4-fluorothiophenol, 4-(5-amino-3-trifluoromethyl-1H-1,2,4-triazol-1-yl)-3-chloro-1-ethylbenzene, 5-(5-amino-3-trifluoromethyl-1H-1,2,4-triazol-1-yl)-4-chloro-2-ethylbenzenesulfonyl chloride, 5-(5-amino-3-trifluoromethyl-1H-1,2,4-triazol-1-yl)-4-chloro-2-ethylbenzenesulfonyl fluoride, 5-(5-amino-3-trifluoromethyl-1H-1,2,4-triazol-1-yl)-4-chloro-2-ethylthiophenol, 2-(5-amino-3-trifluoromethyl-1H-1,2,4-triazol-1-yl)-5-ethyltoluene, 5-(5-amino-3-trifluoromethyl-1H-1,2,4-triazol-1-yl)-2-ethyl-4-methylbenzenesulfonyl chloride, 5-(5-amino-3-trifluoromethyl-1H-1,2,4-triazol-1-yl)-2-ethyl-4-methylbenzenesulfonyl fluoride, 5-(5-amino-3-trifluoromethyl-1H-1,2,4-triazol-1-yl)-2-ethyl-4-methylthiophenol, 2,4-diethyl-1-(5-amino-3-trifluoromethyl-1H-1,2,4-triazol-1-yl)benzene, 5-(5-amino-3-trifluoromethyl-1H-1,2,4-triazol-1-yl)-2,4-diethylbenzenesulfonyl chloride, 5-(5-amino-3-trifluoromethyl-1H-1,2,4-triazol-1-yl)-2,4-diethylbenzenesulfonyl fluoride, 5-(5-amino-3-trifluoromethyl-1H-1,2,4-triazol-1-yl)-2,4-diethylthiophenol, 4-(5-amino-3-trifluoromethyl-1H-1,2,4-triazol-1-yl)-3-isopropyl-1-ethylbenzene, 5-(5-amino-3-trifluoromethyl-1H-1,2,4-triazol-1-yl)-2-ethyl-4-isopropylbenzenesulfonyl chloride, 5-(5-amino-3-trifluoromethyl-1H-1,2,4-triazol-1-yl)-2-ethyl-4-isopropylbenzenesulfonyl fluoride, 5-(5-amino-3-trifluoromethyl-1H-1,2,4-triazol-1-yl)-2-ethyl-4-isopropylthiophenol, 4-(5-amino-3-trifluoromethyl-1H-1,2,4-triazol-1-yl)-3-cyclopropyl-1-ethylbenzene, 5-(5-amino-3-trifluoromethyl-1H-1,2,4-triazol-1-yl)-4-cyclopropyl-2-ethylbenzenesulfonyl chloride, 5-(5-amino-3-trifluoromethyl-1H-1,2,4-triazol-1-yl)-4-cyclopropyl-2-ethylbenzenesulfonyl fluoride, 5-(5-amino-3-trifluoromethyl-1H-1,2,4-triazol-1-yl)-4-cyclopropyl-2-ethylthiophenol, 3-fluoro-4-(5-methylamino-3-trifluoromethyl-1H-1,2,4-triazol-1-yl)-1-ethylbenzene, 2-ethyl-4-fluoro-5-(5-methylamino-3-trifluoromethyl-1H-1,2,4-triazol-1-yl)benzenesulfonyl chloride, 2-ethyl-4-fluoro-5-(5-methylamino-3-trifluoromethyl-1H-1,2,4-triazol-1-yl)benzenesulfonyl fluoride, 2-ethyl-4-fluoro-5-(5-methylamino-3-trifluoromethyl-1H-1,2,4-triazol-1-yl)thiophenol, 3-chloro-4-(5-methylamino-3-trifluoromethyl-1H-1,2,4-triazol-1-yl)-1-ethylbenzene, 4-chloro-2-ethyl-5-(5-methylamino-3-trifluoromethyl-1H-1,2,4-triazol-1-yl)benzenesulfonyl chloride, 4-chloro-2-ethyl-5-(5-methylamino-3-trifluoromethyl-1H-1,2,4-triazol-1-yl)benzenesulfonyl fluoride, 4-chloro-2-ethyl-5-(5-methylamino-3-trifluoromethyl-1H-1,2,4-triazol-1-yl)thiophenol, 5-ethyl-2-(5-methylamino-3-trifluoromethyl-1H-1,2,4-triazol-1-yl)toluene, 2-ethyl-4-methyl-5-(5-methylamino-3-trifluoromethyl-1H-1,2,4-triazol-1-yl)benzenesulfonyl chloride, 2-ethyl-4-methyl-5-(5-methylamino-3-trifluoromethyl-1H-1,2,4-triazol-1-yl)benzenesulfonyl fluoride, 2-ethyl-4-methyl-5-(5- methylamino-3-trifluoromethyl-1H-1,2,4-triazol-1-yl) thiophenol, 2,4-diethyl-1-(5-methylamino-3-trifluoromethyl-1H-1,2,4-triazol-1-yl)benzene, 2,4-diethyl-5-(5-methylamino-3-trifluoromethyl-1H-1,2,4-triazol-1-yl)benzenesulfonyl chloride, 2,4-diethyl-5-(5-methylamino-3-trifluoromethyl-1H-1,2,4-triazol-1-yl)benzenesulfonyl fluoride, 2,4-diethyl-5-(5-methylamino-3-trifluoromethyl-1H-1,2,4-triazol-1-yl)thiophenol, 3-isopropyl-4-(5-methylamino-3-trifluoromethyl-1H-1,2,4-triazol-1-yl)-1-ethylbenzene, 2-ethyl-4-isopropyl-5-(5-methylamino-3-trifluoromethyl-1H-1,2,4-triazol-1-yl)benzenesulfonyl chloride, 2-ethyl-4-isopropyl-5-(5-methylamino-3-trifluoromethyl-1H-1,2,4-triazol-1-yl)benzenesulfonyl fluoride, 2-ethyl-4-isopropyl-5-(5-methylamino-3-trifluoromethyl-1H-1,2,4-triazol-1-yl)thiophenol, 3-cyclopropyl-4-(5-methylamino-3-trifluoromethyl-1H-1,2,4-triazol-1-yl)-1-ethylbenzene, 4-cyclopropyl-2-ethyl-5-(5-methylamino-3-trifluoromethyl-1H-1,2,4-triazol-1-yl)benzenesulfonyl chloride, 4-cyclopropyl-2-ethyl-5-(5-methylamino-3-trifluoromethyl-1H-1,2,4-triazol-1-yl)benzenesulfonyl fluoride, 4-cyclopropyl-2-ethyl-5-(5-methylamino-3-trifluoromethyl-1H-1,2,4-triazol-1-yl)thiophenol, 4-(5-dimethylamino-3-trifluoromethyl-1H-1,2,4-triazol-1-yl)-3-fluoro-1-ethylbenzene, 5-(5-dimethylamino-3-trifluoromethyl-1H-1,2,4-triazol-1-yl)-2-ethyl-4-fluorobenzenesulfonyl chloride, 5-(5-dimethylamino-3-trifluoromethyl-1H-1,2,4-triazol-1-yl)-2-ethyl-4-fluorobenzenesulfonyl fluoride, 5-(5-dimethylamino-3-trifluoromethyl-1H-1,2,4-triazol-1-yl)-2-ethyl-4-fluorothiophenol, 3-chloro-4-(5-dimethylamino-3-trifluoromethyl-1H-1,2,4-triazol-1-yl)-1-ethylbenzene, 4-chloro-5-(5-dimethylamino-3-trifluoromethyl-1H-1,2,4-triazol-1-yl)-2-ethylbenzenesulfonyl chloride, 4-chloro-5-(5-dimethylamino-3-trifluoromethyl-1H-1,2,4-triazol-1-yl)-2-ethylbenzenesulfonyl fluoride, 4-chloro-5-(5-dimethylamino-3-trifluoromethyl-1H-1,2,4-triazol-1-yl)-2-ethylthiophenol, 5-ethyl-2-(5-dimethylamino-3-trifluoromethyl-1H-1,2,4-triazol-1-yl)toluene, 2-ethyl-5-(5-dimethylamino-3-trifluoromethyl-1H-1,2,4-triazol-1-yl)-4-methylbenzenesulfonyl chloride, 2-ethyl-5-(5-dimethylamino-3-trifluoromethyl-1H-1,2,4-triazol-1-yl)-4-methylbenzenesulfonyl fluoride, 2-ethyl-5-(5-dimethylamino-3-trifluoromethyl-1H-1,2,4-triazol-1-yl)-4-methylthiophenol, 2,4-diethyl-1-(5-dimethylamino-3-trifluoromethyl-1H-1,2,4-triazol-1-yl)benzene, 5-(5-dimethylamino-3-trifluoromethyl-1H-1,2,4-triazol-1-yl)-2,4-diethylbenzenesulfonyl chloride, 5-(5-dimethylamino-3-trifluoromethyl-1H-1,2,4-triazol-1-yl)-2,4-diethylbenzenesulfonyl fluoride, 5-(5-dimethylamino-3-trifluoromethyl-1H-1,2,4-triazol-1-yl)-2,4-diethylthiophenol, 4-(5-dimethylamino-3-trifluoromethyl-1H-1,2,4-triazol-1-yl)-3-isopropyl-1-ethylbenzene, 5-(5-dimethylamino-3-trifluoromethyl-1H-1,2,4-triazol-1-yl)-2-ethyl-4-isopropylbenzenesulfonyl chloride, 5-(5-dimethylamino-3-trifluoromethyl-1H-1,2,4-triazol-1-yl)-2-ethyl-4-isopropylbenzenesulfonyl fluoride, 5-(5-dimethylamino-3-trifluoromethyl-1H-1,2,4-triazol-1-yl)-2-ethyl-4-isopropylthiophenol, 3-cyclopropyl-4-(5-dimethylamino-3-trifluoromethyl-1H-1,2,4-triazol-1-yl)-1-ethylbenzene, 4-cyclopropyl-5-(5-dimethylamino-3-trifluoromethyl-1H-1,2,4-triazol-1-yl)-2-ethylbenzenesulfonyl chloride, 4-cyclopropyl-5-(5-dimethylamino-3-trifluoromethyl-1H-1,2,4-triazol-1-yl)-2-ethylbenzenesulfonyl fluoride, 4-cyclopropyl-5-(5-dimethylamino-3-trifluoromethyl-1H-1,2,4-triazol-1-yl)-2-ethylthiophenol, 3-fluoro-4-(3-trifluoromethyl-1H-1,2,4-triazol-1-yl)-1-isopropylbenzene, 4-fluoro-2-isopropyl-5-(3-trifluoromethyl-1H-1,2,4-triazol-1-yl)benzenesulfonyl chloride, 4-fluoro-2-isopropyl-5-(3-trifluoromethyl-1H-1,2,4-triazol-1-yl)benzenesulfonyl fluoride, 4-fluoro-2-isopropyl-5-(3-trifluoromethyl-1H-1,2,4-triazol-1-yl)thiophenol, 3-chloro-4-(3-trifluoromethyl-1H-1,2,4-triazol-1-yl)-1-isopropylbenzene, 4-chloro-2-isopropyl-5-(3-trifluoromethyl-1H-1,2,4-triazol-1-yl)benzenesulfonyl chloride, 4-chloro-2-isopropyl-5-(3-trifluoromethyl-1H-1,2,4-triazol-1-yl)benzenesulfonyl fluoride, 4-chloro-2-isopropyl-5-(3-trifluoromethyl-1H-1,2,4-triazol-1-yl)thiophenol, 5-isopropyl-2-(3-trifluoromethyl-1H-1,2,4-triazol-1-yl)toluene, 2-isopropyl-4-methyl-5-(3-trifluoromethyl-1H-1,2,4-triazol-1-yl)benzenesulfonyl chloride, 2-isopropyl-4-methyl-5-(3-trifluoromethyl-1H-1,2,4-triazol-1-yl)benzenesulfonyl fluoride, 2-isopropyl-4-methyl-5-(3-trifluoromethyl-1H-1,2,4-triazol-1-yl)thiophenol, 5-isopropyl-2-(3-trifluoromethyl-1H-1,2,4-triazol-1-yl)ethylbenzene, 4-ethyl-2-isopropyl-5-(3-trifluoromethyl-1H-1,2,4-triazol-1-yl)benzenesulfonyl chloride, 4-ethyl-2-isopropyl-5-(3-trifluoromethyl-1H-1,2,4-triazol-1-yl)benzenesulfonyl fluoride, 4-ethyl-2-isopropyl-5-(3-trifluoromethyl-1H-1,2,4-triazol-1-yl)thiophenol, 2,4-diisopropyl-1-(3-trifluoromethyl-1H-1,2,4-triazol-1-yl)benzene, 2,4-diisopropyl-5-(3-trifluoromethyl-1H-1,2,4-triazol-1-yl)benzenesulfonyl chloride, 2,4-diisopropyl-5-(3-trifluoromethyl-1H-1,2,4-triazol-1-yl)benzenesulfonyl fluoride, 2,4-diisopropyl-5-(3-trifluoromethyl-1H-1,2,4-triazol-1-yl)thiophenol, 3-cyclopropyl-4-(3-trifluoromethyl-1H-1,2,4-triazol-1-yl)-1-isopropylbenzene, 4-cyclopropyl-2-isopropyl-5-(3-trifluoromethyl-1H-1,2,4-triazol-1-yl)benzenesulfonyl chloride, 4-cyclopropyl-2-isopropyl-5-(3-trifluoromethyl-1H-1,2,4-triazol-1-yl)benzenesulfonyl fluoride, 4-cyclopropyl-2-isopropyl-5-(3-trifluoromethyl-1H-1,2,4-triazol-1-yl)thiophenol, 4-(5-amino-3-trifluoromethyl-1H-1,2,4-triazol-1-yl)-3-fluoro-1-isopropylbenzene, 5-(5-amino-3-trifluoromethyl-1H-1,2,4-triazol-1-yl)-4-fluoro-2-isopropylbenzenesulfonyl chloride, 5-(5-amino-3-trifluoromethyl-1H-1,2,4-triazol-1-yl)-4-fluoro-2-isopropylbenzenesulfonyl fluoride, 5-(5-amino-3-trifluoromethyl-1H-1,2,4-triazol-1-yl)-4-fluoro-2-isopropylthiophenol, 4-(5-amino-3-trifluoromethyl-1H-1,2,4-triazol-1-yl)-3-chloro-1-isopropylbenzene, 5-(5-amino-3-trifluoromethyl-1H-1,2,4-triazol-1-yl)-4-chloro-2-isopropylbenzenesulfonyl chloride, 5-(5-amino-3-trifluoromethyl-1H-1,2,4-triazol-1-yl)-4-chloro-2-isopropylbenzenesulfonyl fluoride, 5-(5-amino-3-trifluoromethyl-1H-1,2,4-triazol-1-yl)-4-chloro-2-isopropylthiophenol, 2-(5-amino-3-trifluoromethyl-1H-1,2,4-triazol-1-yl)-5-isopropyltoluene, 5-(5-amino-3-trifluoromethyl-1H-1,2,4-triazol-1-yl)-2-isopropyl-4-methylbenzenesulfonyl chloride, 5-(5-amino-3-trifluoromethyl-1H-1,2,4-triazol-1-yl)-2-isopropyl-4-methylbenzenesulfonyl fluoride, 5-(5-amino-3-trifluoromethyl-1H-1,2,4-triazol-1-yl)-2-isopropyl-4-methylthiophenol, 2-(5-amino-3-trifluoromethyl-1H-1,2,4-triazol-1-yl)-5-isopropyl-1-ethylbenzene, 5-(5-amino-3-trifluoromethyl-1H-1,2,4-triazol-1-yl)-4-ethyl-2-isopropylbenzenesulfonyl chloride, 5-(5-amino-3-trifluoromethyl-1H-1,2,4-triazol-1-yl)-4-ethyl-2-isopropylbenzenesulfonyl fluoride, 5-(5-amino-3-trifluoromethyl-1H-1,2,4-triazol-1-yl)-4-ethyl-2-isopropylthiophenol, 2,4-diisopropyl-1-(5-amino-3-trifluoromethyl-1H-1,2,4-triazol-1-yl)benzene, 5-(5-amino-3-trifluoromethyl-1H-1,2,4-triazol-1-yl)-2,4-diisopropylbenzenesulfonyl chloride, 5-(5-amino-3-trifluoromethyl-1H-1,2,4-triazol-1-yl)-2,4-diisopropylbenzenesulfonyl fluoride, 5-(5-amino-3-trifluoromethyl-1H-1,2,4-triazol-1-yl)-2,4-diisopropylthiophenol, 4-(5-amino-3-trifluoromethyl-1H-1,2,4-triazol-1-yl)-3-cyclopropyl-1-isopropylbenzene, 5-(5- amino-3-trifluoromethyl-1H-1,2,4-triazol-1-yl)-4-cyclopropyl-2-isopropylbenzenesulfonyl chloride, 5-(5-amino-3-trifluoromethyl-1H-1,2,4-triazol-1-yl)-4-cyclopropyl-2-isopropylbenzenesulfonyl fluoride, 5-(5-amino-3-trifluoromethyl-1H-1,2,4-triazol-1-yl)-4-cyclopropyl-2-isopropylthiophenol, 2-fluoro-4-isopropyl-1-(5-methylamino-3-trifluoromethyl-1H-1,2,4-triazol-1-yl)benzene, 2-methyl-4-fluoro-5-(5-methylamino-3-trifluoromethyl-1H-1,2,4-triazol-1-yl)benzenesulfonyl chloride, 2-methyl-4-fluoro-5-(5-methylamino-3-trifluoromethyl-1H-1,2,4-triazol-1-yl)benzenesulfonyl fluoride, 2-methyl-4-fluoro-5-(5-methylamino-3-trifluoromethyl-1H-1,2,4-triazol-1-yl)thiophenol, 2-chloro-4-isopropyl-1-(5-methylamino-3-trifluoromethyl-1H-1,2,4-triazol-1-yl)benzene, 4-chloro-2-isopropyl-5-(5-methylamino-3-trifluoromethyl-1H-1,2,4-triazol-1-yl)benzenesulfonyl chloride, 4-chloro-2-isopropyl-5-(5-methylamino-3-trifluoromethyl-1H-1,2,4-triazol-1-yl)benzenesulfonyl fluoride, 4-chloro-2-isopropyl-5-(5-methylamino-3-trifluoromethyl-1H-1,2,4-triazol-1-yl)thiophenol, 5-isopropyl-2-(5-methylamino-3-trifluoromethyl-1H-1,2,4-triazol-1-yl)toluene, 2-isopropyl-4-methyl-5-(5-methylamino-3-trifluoromethyl-1H-1,2,4-triazol-1-yl)benzenesulfonyl chloride, 2-isopropyl-4-methyl-5-(5-methylamino-3-trifluoromethyl-1H-1,2,4-triazol-1-yl)benzenesulfonyl fluoride, 2-isopropyl-4-methyl-5-(5-methylamino-3-trifluoromethyl-1H-1,2,4-triazol-1-yl)thiophenol, 5-isopropyl-2-(5-methylamino-3-trifluoromethyl-1H-1,2,4-triazol-1-yl)ethylbenzene, 4-ethyl-2-isopropyl-5-(5-methylamino-3-trifluoromethyl-1H-1,2,4-triazol-1-yl)benzenesulfonyl chloride, 4-ethyl-2-isopropyl-5-(5-methylamino-3-trifluoromethyl-1H-1,2,4-triazol-1-yl)benzenesulfonyl fluoride, 4-ethyl-2-isopropyl-5-(5-methylamino-3-trifluoromethyl-1H-1,2,4-triazol-1-yl)thiophenol, 2,4-diisopropyl-1-(5-methylamino-3-trifluoromethyl-1H-1,2,4-triazol-1-yl)benzene, 2,4-diisopropyl-5-(5-methylamino-3-trifluoromethyl-1H-1,2,4-triazol-1-yl)benzenesulfonyl chloride, 2,4-diisopropyl-5-(5-methylamino-3-trifluoromethyl-1H-1,2,4-triazol-1-yl)benzenesulfonyl fluoride, 2,4-diisopropyl-5-(5-methylamino-3-trifluoromethyl-1H-1,2,4-triazol-1-yl)thiophenol, 2-cyclopropyl-4-isopropyl-1-(5-methylamino-3-trifluoromethyl-1H-1,2,4-triazol-1-yl)benzene, 4-cyclopropyl-2-isopropyl-5-(5-methylamino-3-trifluoromethyl-1H-1,2,4-triazol-1-yl)benzenesulfonyl chloride, 4-cyclopropyl-2-isopropyl-5-(5-methylamino-3-trifluoromethyl-1H-1,2,4-triazol-1-yl)benzenesulfonyl fluoride, 4-cyclopropyl-2-isopropyl-5-(5-methylamino-3-trifluoromethyl-1H-1,2,4-triazol-1-yl)thiophenol, 4-(5-dimethylamino-3-trifluoromethyl-1H-1,2,4-triazol-1-yl)-3-fluoro-1-isopropylbenzene, 5-(5-dimethylamino-3-trifluoromethyl-1H-1,2,4-triazol-1-yl)-4-fluoro-2-isopropylbenzenesulfonyl chloride, 5-(5-dimethylamino-3-trifluoromethyl-1H-1,2,4-triazol-1-yl)-4-fluoro-2-isopropylbenzenesulfonyl fluoride, 5-(5-dimethylamino-3-trifluoromethyl-1H-1,2,4-triazol-1-yl)-4-fluoro-2-isopropylthiophenol, 3-chloro-4-(5-dimethylamino-3-trifluoromethyl-1H-1,2,4-triazol-1-yl)-1-isopropylbenzene, 4-chloro-5-(5-dimethylamino-3-trifluoromethyl-1H-1,2,4-triazol-1-yl)-2-isopropylbenzenesulfonyl chloride, 4-chloro-5-(5-dimethylamino-3-trifluoromethyl-1H-1,2,4-triazol-1-yl)-2-isopropylbenzenesulfonyl fluoride, 4-chloro-5-(5-dimethylamino-3-trifluoromethyl-1H-1,2,4-triazol-1-yl)-2-isopropylthiophenol, 2-(5-dimethylamino-3-trifluoromethyl-1H-1,2,4-triazol-1-yl)-5-isopropyltoluene, 5-(5-dimethylamino-3-trifluoromethyl-1H-1,2,4-triazol-1-yl)-2-isopropyl-4-methylbenzenesulfonyl chloride, 5-(5-dimethylamino-3-trifluoromethyl-1H-1,2,4-triazol-1-yl)-2-isopropyl-4-methylbenzenesulfonyl fluoride, 5-(5-dimethylamino-3-trifluoromethyl-1H-1,2,4-triazol-1-yl)-2-isopropyl-4-methylthiophenol, 2-(5-dimethylamino-3-trifluoromethyl-1H-1,2,4-triazol-1-yl)-5-isopropyl-1-ethylbenzene, 5-(5-dimethylamino-3-trifluoromethyl-1H-1,2,4-triazol-1-yl)-4-ethyl-2-isopropylbenzenesulfonyl chloride, 5-(5-dimethylamino-3-trifluoromethyl-1H-1,2,4-triazol-1-yl)-4-ethyl-2-isopropylbenzenesulfonyl fluoride, 5-(5-dimethylamino-3-trifluoromethyl-1H-1,2,4-triazol-1-yl)-4-ethyl-2-isopropylthiophenol, 2,4-diisopropyl-1-(5-dimethylamino-3-trifluoromethyl-1H-1,2,4-triazol-1-yl)benzene, 5-(5-dimethylamino-3-trifluoromethyl-1H-1,2,4-triazol-1-yl)-2,4-diisopropylbenzenesulfonyl chloride, 5-(5-dimethylamino-3-trifluoromethyl-1H-1,2,4-triazol-1-yl)-2,4-diisopropylbenzenesulfonyl fluoride, 5-(5-dimethylamino-3-trifluoromethyl-1H-1,2,4-triazol-1-yl)-2,4-diisopropylthiophenol, 3-cyclopropyl-4-(5-dimethylamino-3-trifluoromethyl-1H-1,2,4-triazol-1-yl)-1-isopropylbenzene, 4-cyclopropyl-5-(5-dimethylamino-3-trifluoromethyl-1H-1,2,4-triazol-1-yl)-2-isopropylbenzenesulfonyl chloride, 4-cyclopropyl-5-(5-dimethylamino-3-trifluoromethyl-1H-1,2,4-triazol-1-yl)-2-isopropylbenzenesulfonyl fluoride, 4-cyclopropyl-5-(5-dimethylamino-3-trifluoromethyl-1H-1,2,4-triazol-1-yl)-2-isopropylthiophenol, 3-fluoro-4-(3-trifluoromethyl-1H-1,2,4-triazol-1-yl)-1-cyclopropylbenzene, 2-cyclopropyl-4-fluoro-5-(3-trifluoromethyl-1H-1,2,4-triazol-1-yl)benzenesulfonyl chloride, 2-cyclopropyl-4-fluoro-5-(3-trifluoromethyl-1H-1,2,4-triazol-1-yl)benzenesulfonyl fluoride, 2-cyclopropyl-4-fluoro-5-(3-trifluoromethyl-1H-1,2,4-triazol-1-yl)thiophenol, 3-chloro-4-(3-trifluoromethyl-1H-1,2,4-triazol-1-yl)-1-cyclopropylbenzene, 4-chloro-2-cyclopropyl-5-(3-trifluoromethyl-1H-1,2,4-triazol-1-yl)benzenesulfonyl chloride, 4-chloro-2-cyclopropyl-5-(3-trifluoromethyl-1H-1,2,4-triazol-1-yl)benzenesulfonyl fluoride, 4-chloro-2-cyclopropyl-5-(3-trifluoromethyl-1H-1,2,4-triazol-1-yl)thiophenol, 5-cyclopropyl-2-(3-trifluoromethyl-1H-1,2,4-triazol-1-yl)toluene, 2-cyclopropyl-4-methyl-5-(3-trifluoromethyl-1H-1,2,4-triazol-1-yl)benzenesulfonyl chloride, 2-cyclopropyl-4-methyl-5-(3-trifluoromethyl-1H-1,2,4-triazol-1-yl)benzenesulfonyl fluoride, 2-cyclopropyl-4-methyl-5-(3-trifluoromethyl-1H-1,2,4-triazol-1-yl)thiophenol, 5-cyclopropyl-2-(3-trifluoromethyl-1H-1,2,4-triazol-1-yl)-1-ethylbenzene, 2-cyclopropyl-4-ethyl-5-(3-trifluoromethyl-1H-1,2,4-triazol-1-yl)benzenesulfonyl chloride, 2-cyclopropyl-4-ethyl-5-(3-trifluoromethyl-1H-1,2,4-triazol-1-yl)benzenesulfonyl fluoride, 2-cyclopropyl-4-ethyl-5-(3-trifluoromethyl-1H-1,2,4-triazol-1-yl)thiophenol, 5-cyclopropyl-2-(3-trifluoromethyl-1H-1,2,4-triazol-1-yl)-1-isopropylbenzene, 2-cyclopropyl-4-isopropyl-5-(3-trifluoromethyl-1H-1,2,4-triazol-1-yl)benzenesulfonyl chloride, 2-cyclopropyl-4-isopropyl-5-(3-trifluoromethyl-1H-1,2,4-triazol-1-yl)benzenesulfonyl fluoride, 2-cyclopropyl-4-isopropyl-5-(3-trifluoromethyl-1H-1,2,4-triazol-1-yl)thiophenol, 2,4-dicyclopropyl-1-(3-trifluoromethyl-1H-1,2,4-triazol-1-yl)benzene, 2,4-dicyclopropyl-5-(3-trifluoromethyl-1H-1,2,4-triazol-1-yl)benzenesulfonyl chloride, 2,4-dicyclopropyl-5-(3-trifluoromethyl-1H-1,2,4-triazol-1-yl)benzenesulfonyl fluoride, 2,4-dicyclopropyl-5-(3-trifluoromethyl-1H-1,2,4-triazol-1-yl)thiophenol, 4-(5-amino-3-trifluoromethyl-1H-1,2,4-triazol-1-yl)-3-fluoro-1-cyclopropylbenzene, 5-(5-amino-3-trifluoromethyl-1H-1,2,4-triazol-1-yl)-2-cyclopropyl-4-fluorobenzenesulfonyl chloride, 5-(5-amino-3-trifluoromethyl-1H-1,2,4-triazol-1-yl)-2-cyclopropyl-4-fluorobenzenesulfonyl fluoride, 5-(5-amino-3-trifluoromethyl-1H-1,2,4-triazol-1-yl)-2-cyclopropyl-4- fluorothiophenol, 4-(5-amino-3-trifluoromethyl-1H-1,2,4-triazol-1-yl)-3-chloro-1-cyclopropylbenzene, 5-(5-amino-3-trifluoromethyl-1H-1,2,4-triazol-1-yl)-4-chloro-2-cyclopropylbenzenesulfonyl chloride, 5-(5-amino-3-trifluoromethyl-1H-1,2,4-triazol-1-yl)-4-chloro-2-cyclopropylbenzenesulfonyl fluoride, 5-(5-amino-3-trifluoromethyl-1H-1,2,4-triazol-1-yl)-4-chloro-2-cyclopropylthiophenol, 2-(5-amino-3-trifluoromethyl-1H-1,2,4-triazol-1-yl)-5-cyclopropyltoluene, 5-(5-amino-3-trifluoromethyl-1H-1,2,4-triazol-1-yl)-2-cyclopropyl-4-methylbenzenesulfonyl chloride, 5-(5-amino-3-trifluoromethyl-1H-1,2,4-triazol-1-yl)-2-cyclopropyl-4-methylbenzenesulfonyl fluoride, 5-(5-amino-3-trifluoromethyl-1H-1,2,4-triazol-1-yl)-2-cyclopropyl-4-methylthiophenol, 2-(5-amino-3-trifluoromethyl-1H-1,2,4-triazol-1-yl)-5-cyclopropyl-1-ethylbenzene, 5-(5-amino-3-trifluoromethyl-1H-1,2,4-triazol-1-yl)-2-cyclopropyl-4-ethylbenzenesulfonyl chloride, 5-(5-amino-3-trifluoromethyl-1H-1,2,4-triazol-1-yl)-2-cyclopropyl-4-ethylbenzenesulfonyl fluoride, 5-(5-amino-3-trifluoromethyl-1H-1,2,4-triazol-1-yl)-2-cyclopropyl-4-ethylthiophenol, 2-(5-amino-3-trifluoromethyl-1H-1,2,4-triazol-1-yl)-5-cyclopropyl-1-isopropylbenzene, 5-(5-amino-3-trifluoromethyl-1H-1,2,4-triazol-1-yl)-2-cyclopropyl-4-isopropylbenzenesulfonyl chloride, 5-(5-amino-3-trifluoromethyl-1H-1,2,4-triazol-1-yl)-2-cyclopropyl-4-isopropylbenzenesulfonyl fluoride, 5-(5-amino-3-trifluoromethyl-1H-1,2,4-triazol-1-yl)-2-cyclopropyl-4-isopropylthiophenol, 2,4-dicyclopropyl-1-(5-amino-3-trifluoromethyl-1H-1,2,4-triazol-1-yl)benzene, 5-(5-amino-3-trifluoromethyl-1H-1,2,4-triazol-1-yl)-2,4-dicyclopropylbenzenesulfonyl chloride, 5-(5-amino-3-trifluoromethyl-1H-1,2,4-triazol-1-yl)-2,4-dicyclopropylbenzenesulfonyl fluoride, 5-(5-amino-3-trifluoromethyl-1H-1,2,4-triazol-1-yl)-2,4-dicyclopropylthiophenol, 4-cyclopropyl-2-fluoro-1-(5-methylamino-3-trifluoromethyl-1H-1,2,4-triazol-1-yl)benzene, 2-cyclopropyl-4-fluoro-5-(5-methylamino-3-trifluoromethyl-1H-1,2,4-triazol-1-yl)benzenesulfonyl chloride, 2-cyclopropyl-4-fluoro-5-(5-methylamino-3-trifluoromethyl-1H-1,2,4-triazol-1-yl)benzenesulfonyl chloride, 2-cyclopropyl-4-fluoro-5-(5-methylamino-3-trifluoromethyl-1H-1,2,4-triazol-1-yl)thiophenol, 2-chloro-4-cyclopropyl-1-(5-methylamino-3-trifluoromethyl-1H-1,2,4-triazol-1-yl)benzene, 4-chloro-2-cyclopropyl-5-(5-methylamino-3-trifluoromethyl-1H-1,2,4-triazol-1-yl)benzenesulfonyl chloride, 4-chloro-2-cyclopropyl-5-(5-methylamino-3-trifluoromethyl-1H-1,2,4-triazol-1-yl)benzenesulfonyl fluoride, 4-chloro-2-cyclopropyl-5-(5-methylamino-3-trifluoromethyl-1H-1,2,4-triazol-1-yl)thiophenol, 3-cyclopropyl-6-(5-methylamino-3-trifluoromethyl-1H-1,2,4-triazol-1-yl)toluene, 2-cyclopropyl-4-methyl-5-(5-methylamino-3-trifluoromethyl-1H-1,2,4-triazol-1-yl)benzenesulfonyl chloride, 2-cyclopropyl-4-methyl-5-(5-methylamino-3-trifluoromethyl-1H-1,2,4-triazol-1-yl)benzenesulfonyl fluoride, 2-cyclopropyl-4-methyl-5-(5-methylamino-3-trifluoromethyl-1H-1,2,4-triazol-1-yl)thiophenol, 3-cyclopropyl-6-(5-methylamino-3-trifluoromethyl-1H-1,2,4-triazol-1-yl)-1-ethylbenzene, 4-ethyl-2-cyclopropyl-5-(5-methylamino-3-trifluoromethyl-1H-1,2,4-triazol-1-yl)benzenesulfonyl chloride, 4-ethyl-2-cyclopropyl-5-(5-methylamino-3-trifluoromethyl-1H-1,2,4-triazol-1-yl)benzenesulfonyl fluoride, 4-ethyl-2-cyclopropyl-5-(5-methylamino-3-trifluoromethyl-1H-1,2,4-triazol-1-yl)thiophenol, 4-cyclopropyl-2-isopropyl-1-(5-methylamino-3-trifluoromethyl-1H-1,2,4-triazol-1-yl)benzene, 2-cyclopropyl-4-isopropyl-5-(5-methylamino-3-trifluoromethyl-1H-1,2,4-triazol-1-yl) benzenesulfonyl chloride, 2-cyclopropyl-4-isopropyl-5-(5-methylamino-3-trifluoromethyl-1H-1,2,4-triazol-1-yl) benzenesulfonyl fluoride, 2-cyclopropyl-4-isopropyl-5-(5-methylamino-3-trifluoromethyl-1H-1,2,4-triazol-1-yl) thiophenol, 2,4-dicyclopropyl-1-(5-methylamino-3-trifluoromethyl-1H-1,2,4-triazol-1-yl)benzene, 2,4-dicyclopropyl-5-(5-methylamino-3-trifluoromethyl-1H-1,2,4-triazol-1-yl)benzenesulfonyl chloride, 2,4-dicyclopropyl-5-(5-methylamino-3-trifluoromethyl-1H-1,2,4-triazol-1-yl) benzenesulfonyl fluoride, 2,4-dicyclopropyl-5-(5-methylamino-3-trifluoromethyl-1H-1,2,4-triazol-1-yl) thiophenol, 4-(5-dimethylamino-3-trifluoromethyl-1H-1,2,4-triazol-1-yl)-3-fluoro-1-cyclopropylbenzene, 5-(5-dimethylamino-3-trifluoromethyl-1H-1,2,4-triazol-1-yl)-2-cyclopropyl-4-fluoro-1-benzenesulfonyl chloride, 5-(5-dimethylamino-3-trifluoromethyl-1H-1,2,4-triazol-1-yl)-2-cyclopropyl-4-fluorobenzenesulfonyl fluoride, 5-(5-dimethylamino-3-trifluoromethyl-1H-1,2,4-triazol-1-yl)-2-cyclopropyl-4-fluorothiophenol, 3-chloro-4-(5-dimethylamino-3-trifluoromethyl-1H-1,2,4-triazol-1-yl)-1-cyclopropylbenzene, 4-chloro-2-cyclopropyl-5-(5-dimethylamino-3-trifluoromethyl-1H-1,2,4-triazol-1-yl) benzenesulfonyl chloride, 4-chloro-2-cyclopropyl-5-(5-dimethylamino-3-trifluoromethyl-1H-1,2,4-triazol-1-yl) benzenesulfonyl fluoride, 4-chloro-2-cyclopropyl-5-(5-dimethylamino-3-trifluoromethyl-1H-1,2,4-triazol-1-yl) thiophenol, 5-cyclopropyl-2-(5-dimethylamino-3-trifluoromethyl-1H-1,2,4-triazol-1-yl)toluene, 2-cyclopropyl-5-(5-dimethylamino-3-trifluoromethyl-1H-1,2,4-triazol-1-yl)-4-methylbenzenesulfonyl chloride, 2-cyclopropyl-5-(5-dimethylamino-3-trifluoromethyl-1H-1,2,4-triazol-1-yl)-4-methylbenzenesulfonyl fluoride, 2-cyclopropyl-5-(5-dimethylamino-3-trifluoromethyl-1H-1,2,4-triazol-1-yl)-4-methylthiophenol, 5-cyclopropyl-2-(5-dimethylamino-3-trifluoromethyl-1H-1,2,4-triazol-1-yl)-1-ethylbenzene, 2-cyclopropyl-5-(5-dimethylamino-3-trifluoromethyl-1H-1,2,4-triazol-1-yl)-4-ethylbenzenesulfonyl chloride, 2-cyclopropyl-5-(5-dimethylamino-3-trifluoromethyl-1H-1,2,4-triazol-1-yl)-4-ethylbenzenesulfonyl fluoride, 2-cyclopropyl-5-(5-dimethylamino-3-trifluoromethyl-1H-1,2,4-triazol-1-yl)-4-ethylthiophenol, 5-cyclopropyl-2-(5-dimethylamino-3-trifluoromethyl-1H-1,2,4-triazol-1-yl)-1-isopropylbenzene, 2-cyclopropyl-5-(5-dimethylamino-3-trifluoromethyl-1H-1,2,4-triazol-1-yl)-4-isopropylbenzenesulfonyl chloride, 2-cyclopropyl-5-(5-dimethylamino-3-trifluoromethyl-1H-1,2,4-triazol-1-yl)-4-isopropylbenzenesulfonyl fluoride, 2-cyclopropyl-5-(5-dimethylamino-3-trifluoromethyl-1H-1,2,4-triazol-1-yl)-4-isopropylthiophenol, 2,4-dicyclopropyl-1-(5-dimethylamino-3-trifluoromethyl-1H-1,2,4-triazol-1-yl)benzene, 2,4-dicyclopropyl-5-(5-dimethylamino-3-trifluoromethyl-1H-1,2,4-triazol-1-yl)benzenesulfonyl chloride, 2,4-dicyclopropyl-5-(5-dimethylamino-3-trifluoromethyl-1H-1,2,4-triazol-1-yl)benzenesulfonyl fluoride, 2,4-dicyclopropyl-5-(5-dimethylamino-3-trifluoromethyl-1H-1,2,4-triazol-1-yl)thiophenol.

Then, description is made on the process for production of an aryl (1H-1,2,4-triazol-1-yl) compound represented by the general formula (1).

The process for production of an aryl (1H-1,2,4-triazol-1-yl) compound represented by the general formula (1) includes the followings:

a process for production of a (1H-1,2,4-triazol-1-yl)benzene compound represented by the general formula (5) (hereinafter, this compound is expressed simply as "unsubstituted compound", in some cases), which comprises reacting a triazole compound represented by the general formula (2) with a compound represented by the general formula (3) or the general formula (4) in the presence of a copper catalyst (this process is described in the above [5]), a process for production of a (1H-1,2,4-triazol-1-yl)toluene compound represented by the general formula (8), which comprises reacting a triazole compound represented by the general formula (2) with a 4-substituted-halobenzene compound represented by the general formula (6) in the presence of a base to obtain a 4-substituted (1H-1,2,4-triazol-1-yl) benzene compound represented by the general formula (7) and then reducing the 4-substituted (1H-1,2,4-triazol-1-yl) benzene compound represented by the general formula (7) (this process is described in the above [12] and [14]), a process for production of a (1H-1,2,4-triazol-1-yl)toluene compound represented by the general formula (8), which comprises reducing a 4-cyano-1-(1H-1,2,4-triazol-1-yl)benzene compound represented by the general formula (7') to obtain a diethylamine compound represented by the general formula (9) and further reducing the diethylamine compound represented by the general formula (9) (this process is described in the above [19]), a process for production of a 3-(1H-1,2,4-triazol-1-yl)benzenesulfonyl halide compound represented by the general formula (10), which comprises reacting a (1H-1,2,4-triazol-1-yl)benzene compound represented by the general formula (5) with a halosulfonylating agent (this process is described in the above [22]), and a process for production of a 3-(1H-1,2,4-triazol-1-yl)phenylmercaptan compound represented by the general formula (11), which comprises reducing a 3-(1H-1,2,4-triazol-1-yl) benzenesulfonyl halide compound represented by the general formula (10) (this process is described in the above [24]).

Here, the compounds represented by the general formula (5), the general formula (8), the general formula (10) and the general formula (11) are all included in the present invention compound represented by the general formula (1).

First, description is made on the process for production of an unsubstituted compound represented by the general formula (5) by a coupling reaction.

In the general formula (5), the general formula (2), the general formula (3) and the general formula (4), R, $A_1$ and $A_2$ have the same definitions as given previously. Also, the unsubstituted compound represented by the general formula (5), the triazole compound represented by the general formula (2) used as a raw material of the coupling, the boronic acid compound represented by the general formula (3) and the boroxine compound represented by the general formula (4) are all known compounds.

In the coupling reaction, a triazole compound represented by the general formula (2) is reacted with a boronic acid compound represented by the general formula (3) or a boroxine compound represented by the general formula (4), whereby an intended unsubstituted compound represented by the general formula (5) can be produced.

In the coupling reaction, the compound to be reacted with the triazole compound represented by the general formula (2) is ordinarily selected from a boronic acid compound represented by the general formula (3) and a boroxine compound represented by the general formula (4); however, a mixture thereof may be used as the compound to be reacted with the triazole compound.

In the coupling reaction, the molar ratio of the triazole compound represented by the general formula (2) and the boronic acid compound represented by the general formula (3) or the boroxine compound represented by the general formula (4) may be any molar ratio, and intended reaction proceeds. However, when the triazole compound represented by the general formula (2) is reacted with the boronic acid compound represented by the general formula (3), the boronic acid compound represented by the general formula (3) is used, for example, ordinarily by 0.1 to 10.0 mols, preferably by 0.33 to 3.0 mols per 1 mol of the triazole compound represented by the general formula (2). When the triazole compound represented by the general formula (2) is reacted with the boroxine compound represented by the general formula (4), the boroxine compound represented by the general formula (4) is used, for example, ordinarily by 0.033 to 3.33 mols, preferably by 0.1 to 1.0 mol per 1 mol of the triazole compound represented by the general formula (2).

In the coupling reaction, a copper catalyst is used. The copper catalyst used in the reaction may be any copper compound as long as it can give rise to the coupling reaction. However, as specific examples, there can be mentioned copper (metallic copper), copper (II) acetate, copper (I) acetate, copper (II) oxide, copper (I) oxide, copper (II) chloride, copper (I) chloride, copper (II) sulfate and copper (II) nitrate. Copper (metallic copper), copper (II) acetate, copper (I) acetate, copper (II) oxide and copper (I) oxide are used preferably, and copper (metallic copper) and copper (II) acetate are used more preferably, from the standpoints of the low reactivity of counter anion, the high availability and easy handling, the reactivity, etc. These copper catalysts may be used singly or in admixture of any mixing ratio. These copper catalysts are known compounds. The use amount of the copper catalyst in the coupling reaction may be any molar ratio relative to the triazole compound represented by the general formula (2), and intended reaction proceeds. However, the amount is, for example, ordinarily 0.001 to 1.0 mol, preferably 0.01 to 0.5 mol, more preferably 0.05 to 0.2 mol per 1 mol of the triazole compound represented by the general formula (2).

The coupling reaction may be conducted in the absence of a base. However, use of a base is preferred. As specific examples of the base usable in the reaction, there can be mentioned tertiary amine compounds such as pyridine, diisopropylethylamine, triethylamine and the like; and inorganic bases such as alkali metal hydroxide (e.g. sodium hydroxide), alkali metal carbonate (e.g. potassium carbonate) and the like. These bases may be used singly or in admixture of any mixing ratio. Tertiary amine compounds such as pyridine, diisopropylethylamine, triethylamine and the like are used preferably, and pyridine and diisopropylethylamine are used more preferably, from the standpoints of the high availability and easy handling, the reactivity, etc. These bases are known compounds. The use amount of the base in the coupling reaction may be any molar ratio relative to the triazole compound represented by the general formula (2), and intended reaction proceeds. However, the amount is, for example, ordinarily 0.1 to 10 mols, preferably 0.33 to 3.0 mols, more preferably 1.0 to 2.0 mols per 1 mol of the triazole compound represented by the general formula (2).

The coupling reaction may be conducted in a solvent-free state. However, a solvent is preferably used for smooth progress of the reaction. The solvent usable in the coupling reaction may be any solvent as long as it does not hinder the reaction. There can be mentioned, for example, aprotic polar solvents such as N,N-dimethylformamide, N,N-dimethylacetamide, acetonitrile, acetone, propylene carbonate and the like; alcohols such as ethanol, isopropanol, ethylene glycol and the like; ethers such as diphenyl ether, tetrahydrofuran and the like; aromatic hydrocarbons such as toluene, xylene and the like; and aliphatic hydrocarbons such as pentane, n-hexane and the like. Preferred are aprotic polar solvents such as N,N-dimethylformamide, N,N-dimethylacetamide, acetonitrile, acetone, propylene carbonate and the like, and particularly preferred is N,N-dimethylformamide. The solvents may be used singly or in admixture of any mixing ratio. The use amount of the solvent may be such an amount that enables sufficient stirring of the reaction system; however, the amount may be ordinarily 0.05 to 10 liters, preferably 0.3 to 2 liters per 1 mol of the triazole compound represented by the general formula (2).

The reaction temperature of the coupling reaction is, for example, 0° C. to the reflux temperature of the solvent used, preferably 10 to 100° C.

The reaction time of the coupling reaction is not particularly restricted; however, it is preferably 1 hour to 30 hours from the standpoints of the suppression of by-product formation, etc.

Next, description is made on the process for production of a 4-substituted (1H-1,2,4-triazol-1-yl)benzene compound represented by the general formula (7), which comprises reacting a triazole compound represented by the general formula (2) with a 4-substituted halobenzene compound represented by the general formula (6) in the presence of a base.

In the general formula (7), the general formula (2) and the general formula (6), $A_1$ and $A_2$ have the same definitions as given above; X is a halogen atom such as chlorine atom, fluorine atom, bromine atom or the like; and Y is an electron withdrawing group having a carbon atom bonding to benzene ring (C1 unit), such as cyano group, formyl group, carboxyl group or metal salt thereof, alkoxycarbonyl group or the like.

In the nucleophilic substitution reaction, the use amount of the 4-substituted halobenzene compound represented by the general formula (6) may be any molar ratio, and intended reaction proceeds; however, the amount is, for example, ordinarily 0.1 to 10.0 mols, preferably 0.33 to 3.0 mols per 1 mol of the triazole compound represented by the general formula (2).

A base is used in the nucleophilic substitution reaction. As specific examples of the base used in the nucleophilic substitution reaction, there can be mentioned alkali metal carbonates such as potassium carbonate, sodium carbonate, potassium hydrogencarbonate, sodium hydrogencarbonate and the like; alkali metal hydroxides such as sodium hydroxide, potassium hydroxide and the like; and tertiary amine compounds such as pyridine, diisopropylethylamine, triethylamine and the like. These bases may be used singly or in admixture of any mixing ratio. Preferred are alkali metal carbonates such as potassium carbonate, sodium carbonate, potassium hydrogencarbonate, sodium hydrogencarbonate and the like and more preferred is potassium carbonate, from the standpoints of the availability, the easy handling, the reactivity, etc. These bases are known compounds. In the nucleophilic substitution reaction, the use amount of the base may be any molar ratio to the triazole compound represented by the general formula (2), and intended reaction proceeds; however, the amount is, for example, ordinarily 0.1 to 10.0 mols, preferably 0.33 to 3.0 mols, more preferably 1.0 to 2.0 mols per 1 mol of the triazole compound represented by the general formula (2).

The nucleophilic substitution reaction may be conducted in a solvent-free state. However, a solvent is preferably used for smooth progress of the reaction. The solvent usable in the nucleophilic substitution reaction may be any solvent as long as it does not hinder the reaction. There can be mentioned, for example, aprotic polar solvents such as N,N-dimethylformamide, N,N-dimethylacetamide, acetonitrile, acetone, propylene carbonate and the like; alcohols such as ethanol, isopropanol, ethylene glycol and the like; ethers such as diphenyl ether, tetrahydrofuran and the like; aromatic hydrocarbons such as toluene, xylene and the like; and aliphatic hydrocarbons such as pentane, n-hexane and the like. Preferred are aprotic polar solvents such as N,N-dimethylformamide, N,N-dimethylacetamide, acetonitrile, acetone, propylene carbonate and the like, and particularly preferred is N,N-dimethylformamide. These solvents may be used singly or as a mixed solvent of any mixing ratio. The use amount of the solvent may be such an amount that can cause sufficient stirring of the reaction system; however, it is ordinarily 0.05 to 10 liters, preferably 0.3 to 2 liters per 1 mol of the triazole compound represented by the general formula (2).

The reaction temperature of the nucleophilic substitution reaction is, for example, 0° C. to the reflux temperature of the solvent used, preferably 20 to 150° C.

The reaction time of the nucleophilic substitution reaction is not particularly restricted, but is preferably 1 hour to 30 hours in view of, for example, the suppression of by-product formation.

Next, description is made on the process for production of a 4-(1H-1,2,4-triazol-1-yl)toluene compound represented by the general formula (8), which comprises reducing a 4-substituted (1H-1,2,4-triazol-1-yl)benzene compound represented by the general formula (7). Incidentally, in the general formula (8) and the general formula (7), $A_1$, $A_2$ and Y have the same definitions as given above.

A heterogeneous metal catalyst is preferably used in the reduction reaction. As specific examples of the heterogeneous metal catalyst used in the reduction reaction, there can be mentioned palladium carbon, palladium-loaded alumina, palladium-loaded barium sulfate, palladium-loaded calcium carbonate, platinum-loaded carbon, platinum-loaded alumina, rhodium-loaded carbon, ruthenium-loaded carbon, nickel-loaded carbon and Raney nickel. Preferably used are palladium carbon and palladium-loaded alumina, which have high reactivity and are easy in recovery of expensive noble metal catalyst, and palladium carbon is preferred from the standpoints of the availability, the easy handling, the reactivity, etc. These heterogeneous metal catalysts are known compounds. The use amount of the heterogeneous metal catalyst in the reduction reaction may be any amount relative to the 4-substituted (1H-1,2,4-triazol-1-yl)benzene compound represented by the general formula (7), and intended reaction proceeds; however, the amount in terms of the metal weight in catalyst is, for example, ordinarily 0.1 to 10.0 times, preferably 0.1 to 5 times of the weight of the 4-substituted (1H-1,2,4-triazol-1-yl)benzene compound represented by the general formula (7).

A reducing agent is used in the reduction reaction. As specific examples of the reducing agent used in the reaction, ammonium formate and hydrogen can be mentioned. Ammonium formate is preferred from the standpoints of the availability, the easy handling, the reactivity, etc. These reducing agents are known compounds. In the reduction reaction, the use amount of the reducing agent may be any amount relative to the 4-substituted (1H-1,2,4-triazol-1-yl)benzene compound represented by the general formula (7), and intended reaction proceeds; however, the amount is, for example, ordinarily 0.1 to 20.0 mols, preferably 1.0 to 10 mols per 1 mol of the 4-substituted (1H-1,2,4-triazol-1-yl)benzene compound represented by the general formula (7).

The reduction reaction may be conducted in a solvent-free state. However, a solvent is preferably used for smooth progress of the reaction. The solvent usable in the reduction reaction may be any solvent as long as it does not hinder the reaction. There can be mentioned, for example, alcohols such as methanol, ethanol, isopropanol, ethylene glycol and the like; aprotic polar solvents such as N,N-dimethylformamide, N,N-dimethylacetamide, acetonitrile, acetone, propylene carbonate and the like; ethers such as diphenyl ether, tetrahydrofuran and the like; aromatic hydrocarbons such as toluene, xylene and the like; and aliphatic hydrocarbons such as pentane, n-hexane and the like. Preferred are alcohols such as methanol, ethanol, isopropanol, ethylene glycol and the like, and particularly preferred is methanol. These solvents may be used singly or in admixture of any mixing ratio. The use amount of the solvent may be such an amount that can cause sufficient stirring of the reaction system; however, the amount is ordinarily 0.05 to 10 liters, preferably 0.3 to 2 liters per 1 mol of the 4-substituted (1H-1,2,4-triazol-1-yl)benzene compound represented by the general formula (7).

The reaction temperature of the reduction reaction is, for example, 0° C. to the reflux temperature of the solvent used, preferably 10 to 100° C.

The reaction time of the reduction reaction is not particularly restricted; however, it is preferably 1 hour to 100 hours from the standpoints of the suppression of by-product formation, etc.

Then, description is made on the process for production of a 4-(1H-1,2,4-triazol-1-yl)toluene compound represented by the general formula (8), which comprises reducing a 4-cyano-(1H-1,2,4-triazol-1-yl)benzene compound represented by the general formula (7') in the presence of a Raney nickel catalyst to obtain a diethylamine compound represented by the general formula (9) and then further reducing the compound.

Description is made first on the process for production of a diethylamine compound represented by the general formula (9) by reducing a 4-cyano-(1H-1,2,4-triazol-1-yl)benzene compound represented by the general formula (7') in the presence of a Raney nickel catalyst. Incidentally, in the general formula (9) and the general formula (7'), $A_1$ and $A_2$ have the same definitions as given above, and Et is an ethyl group.

A Raney nickel catalyst is used in the reaction. Preferably, the Raney nickel catalyst is used after activation by an appropriate method. The use amount of the Raney nickel catalyst in the reaction may be any amount relative to the 4-cyano-(1H-1,2,4-triazol-1-yl)benzene compound represented by the general formula (7'), and intended reaction proceeds; however, the amount in terms of the metal weight of the catalyst is, for example, ordinarily 1.0 to 10.0 times, preferably 2.0 to 7.0 times of the use weight of the 4-cyano-(1H-1,2,4-triazol-1-yl)benzene compound represented by the general formula (7').

The reaction may be conducted in a solvent-free state, but a solvent is preferably used for smooth progress of the reaction. The solvent used in the reduction reaction may be any solvent as long as it does not hinder the reaction. There can be mentioned, for example, alcohols such as methanol, ethanol, isopropanol, ethylene glycol and the like; aprotic polar solvents such as N,N-dimethylformamide, N,N-dimethylacetamide, acetonitrile, acetone, propylene carbonate and the like; ethers such as diphenyl ether, tetrahydrofuran and the like; aromatic hydrocarbons such as toluene, xylene and the like; and aliphatic hydrocarbons such as pentane, n-hexane and the like. Preferred are alcohols such as methanol, ethanol, isopropanol, ethylene glycol and the like, and particularly preferred is ethanol. These solvents may be used singly or in admixture of any mixing ratio. The use amount of the solvent may be such an amount that can cause sufficient stirring of the reaction system; however, the amount is ordinarily 0.05 to 10 liters, preferably 0.3 to 2 liters per 1 mol of the 4-cyano-(1H-1,2,4-triazol-1-yl)benzene compound represented by the general formula (7').

The reaction temperature of the reaction is, for example, 0° C. to the reflux temperature of the solvent used, preferably 10 to 100° C.

The reaction time of the reaction is not particularly restricted; however, it is preferably 1 hour to 100 hours from the standpoints of the suppression of by-product formation, etc.

Next, description is made on the process for production of a 4-(1H-1,2,4-triazol-1-yl)toluene compound represented by the general formula (8), which comprises reducing a diethylamine compound represented by the general formula (9). Incidentally, in the general formula (8) and the general formula (9), $A_1$, $A_2$ and Et have the same definitions as given above.

A heterogeneous metal catalyst is used in the reduction reaction. As specific examples of the heterogeneous metal catalyst used in the reaction, there can be mentioned palladium (II) hydroxide carbon, palladium carbon, palladium-loaded alumina, palladium-loaded barium sulfate, palladium-loaded calcium carbonate, platinum-loaded carbon, platinum-loaded alumina, rhodium-loaded carbon, ruthenium-loaded carbon, nickel-loaded carbon and Raney nickel. Preferably used is palladium (II) hydroxide carbon which has high reactivity and is easy in recovery of expensive noble metal catalyst after the reaction. These heterogeneous metal catalysts are known compounds. The use amount of the heterogeneous metal catalyst in the reduction reaction may be any amount relative to the diethylamine compound represented by the general formula (9), and intended reaction proceeds; however, the amount in terms of the metal weight in catalyst is, for example, ordinarily 0.001 to 1.0 time, preferably 0.01 to 0.1 time, more preferably 0.01 to 0.05 time of the use weight of the dimethylamine compound represented by the general formula (9).

A reducing agent is used in the reduction reaction. As specific examples of the reducing agent used in the reaction, ammonium formate and hydrogen can be mentioned. Hydrogen is preferred from the standpoints of the availability, the easy handling, the reactivity, etc. These reducing agents are known compounds. In the reduction reaction, the use amount of the reducing agent may be any molar ratio relative to the dimethylamine compound represented by the general formula (9), and intended reaction proceeds; however, the amount is, for example, ordinarily 0.1 to 20.0 mols, preferably 1.0 to 10 mols per 1 mol of the dimethylamine compound represented by the general formula (9).

The reduction reaction may be conducted in a solvent-free state. However, a solvent is preferably used for smooth progress of the reaction. The solvent usable in the reduction reaction may be any solvent as long as it does not hinder the reaction. There can be mentioned, for example, alcohols such as methanol, ethanol, isopropanol, ethylene glycol and the like; aprotic polar solvents such as N,N-dimethylformamide, N,N-dimethylacetamide, acetonitrile, acetone, propylene carbonate and the like; ethers such as diphenyl ether, tetrahydrofuran and the like; aromatic hydrocarbons such as toluene, xylene and the like; and aliphatic hydrocarbons such as pentane, n-hexane and the like. Preferred are alcohols such as methanol, ethanol, isopropanol, ethylene glycol and the like, and particularly preferred is methanol. These solvents may be used singly or in admixture of any mixing ratio. The use amount of the solvent may be such an amount that can cause sufficient stirring of the reaction system; however, the amount is ordinarily 0.05 to 10 liters, preferably 0.3 to 2 liters per 1 mol of the diethylamine compound represented by the general formula (9).

The reaction temperature of the reduction reaction is, for example, 0° C. to the reflux temperature of the solvent used, preferably 10 to 100° C.

The reaction time of the reduction reaction is not particularly restricted; however, it is preferably 1 hour to 100 hours from the standpoints of the suppression of by-product formation, etc.

Then, description is made on the process for production of a 3-(1H-1,2,4-triazol-1-yl)benzenesulfonyl halide compound represented by the general formula (10), which comprises subjecting a (1H-1,2,4-triazol-1-yl)benzene compound represented by the general formula (5) to halosulfonylation. Incidentally, in the general formula (10) and the general formula (5), R, $A_1$, $A_2$ and X have the same definitions as given above.

A halosulfonylating agent is used in the halosulfonylation reaction. As specific examples of the halosulfonylating agent used in the reaction, there can be mentioned halosulfonic acid compounds such as chlorosulfonic acid, bromosulfonic acid and the like. These halosulfonylating agents may be used singly or in admixture of any mixing ratio. Preferred is chlorosulfonic acid from the standpoints of the availability, the easy handling, the reactivity, etc. These halosulfonylating agents are known compounds. The use amount of the halosulfonylating agent in the halosulfonylation reaction may be any molar ratio, and intended reaction proceeds; however, the amount is, for example, ordinarily 0.033 to 100.0 mols, preferably 1.0 to 10.0 mols per 1 mol of the (1H-1,2,4-triazol-1-yl)benzene compound represented by the general formula (5).

The halosulfonylation reaction may be conducted in a solvent-free state. However, a solvent may be used for smooth progress of the reaction. The solvent usable in the halosulfonylation may be any solvent as long as it does not hinder the reaction. There can be mentioned, for example, halogenated hydrocarbons such as dichloroethane, chloroform and the like; aprotic polar solvents such as N,N-dimethylformamide, N,N-dimethylacetamide, acetonitrile, acetone, propylene carbonate and the like; ethers such as phenyl ether, tetrahydrofuran and the like; aromatic hydrocarbons such as toluene, xylene and the like; and aliphatic hydrocarbons such as pentane, n-hexane and the like. Preferred are halogenated hydrocarbons such as dichloroethane, chloroform and the like, and particularly preferred is dichloroethane. These solvents may be used singly or in admixture of any mixing ratio. The use amount of the solvent may be any amount as long as it can cause sufficient stirring of the reaction system. However, the amount is ordinarily 0.05 to 10 liters, preferably 0.3 to 2 liters per 1 mol of the (1H-1,2,4-triazol-1-yl)benzene compound represented by the general formula (5).

The reaction temperature of the halosulfonylation reaction is, for example, 0° C. to the reflux temperature of the solvent used, preferably 10 to 100° C.

The reaction time of the halosulfonylation reaction is not particularly restricted; however, it is preferably 1 hour to 30 hours from the standpoints of the suppression of by-product formation, etc.

Then, description is made on the process for production of a 3-(1H-1,2,4-triazol-1-yl)phenylmercaptan compound represented by the general formula (11), which comprises reducing a 3-(1H-1,2,4-triazol-1-yl)benzenesulfonyl halide compound represented by the general formula (10). Incidentally, in the general formula (11) and the general formula (10), R, $A_1$, $A_2$ and X have the same definitions as given above.

A reducing agent is used in the reduction reaction. As specific examples of the reducing agent used in the reaction, metal compounds of zinc, tin, iron, etc. can be mentioned. These reducing agents may be used singly or in admixture of any mixing ratio. Zinc is preferred from the standpoints of the availability, the easy handling, the reactivity, etc. These reducing agents are known compounds.

In the reduction reaction, the use amount of the reducing agent may be any molar ratio, and intended reaction proceeds; however, the amount is, for example, ordinarily 0.1 to 100.0 mols, preferably 1.0 to 10.0 mols per 1 mol of the 3-(1H-1,2,4-triazol-1-yl)benzenesulfonyl halide compound represented by the general formula (10).

An acid is preferably used in the reduction reaction. As specific examples of the acid used in the reaction, there can be mentioned inorganic acids such as hydrochloric acid, sulfuric acid, nitric acid, phosphoric acid and the like; Lewis acids such as aluminum chloride, poly-phosphoric acid and the like; organic acids such as acetic acid and the like; and solid acids such as montmorillonite K-10 and the like. These acids may be used singly or in admixture of any mixing ratio. Preferred are inorganic acids such as hydrochloric acid, sulfuric acid, nitric acid and the like from the standpoints of the availability, the easy handling, the reactivity, etc., and more preferred is hydrochloric acid. Incidentally, these acids are known compounds.

The use amount of the acid in the reduction reaction may be any molar ratio, and intended reaction proceeds; however, the amount is, for example, ordinarily 0.066 to 200.0 mols, preferably 2.0 to 20.0 mols per 1 mol of the 3-(1H-1,2,4-triazol-1-yl)benzenesulfonyl halide compound represented by the general formula (10).

The reduction reaction may be conducted in a solvent-free state. However, a solvent may be used for smooth progress of the reaction. The solvent usable in the reduction reaction may be any solvent as long as it does not hinder the reaction. There can be mentioned, for example, alcohols such as ethanol, isopropanol, ethylene glycol and the like; halogenated hydrocarbons such as dichloroethane, chloroform and the like; aprotic polar solvents such as N,N-dimethylformamide, N,N-dimethylacetamide, acetonitrile, acetone, propylene carbonate and the like; ethers such as phenyl ether, tetrahydrofuran and the like; aromatic hydrocarbons such as toluene, xylene and the like; and aliphatic hydrocarbons such as pentane, n-hexane and the like. Preferred are alcohols such as ethanol, isopropanol, ethylene glycol and the like, and particularly preferred is ethanol. These solvents may be used singly or in admixture of any mixing ratio. The use amount of the solvent may be any amount as long as it can cause sufficient stirring of the reaction system. However, the amount is ordinarily 0.05 to 10 liters, preferably 0.3 to 2 liters per 1 mol of the 3-(1H-1,2,4-triazol-1-yl)benzenesulfonyl halide compound represented by the general formula (10).

The reaction temperature of the reduction reaction is, for example, 0° C. to the reflux temperature of the solvent used, preferably 10 to 100° C.

The reaction time of the reduction reaction is not particularly restricted; however, it is preferably 1 hour to 30 hours from the standpoints of the suppression of by-product formation, etc.

As described above, the process of the present invention enables production of an aryl (1H-1,2,4-triazol-1-yl) compound represented by the general formula (1) at a high selectivity under mild conditions easily employable industrially, without using any special reaction equipment. The obtained aryl (1H-1,2,4-triazol-1-yl) compound represented by the general formula (1) is useful as an intermediate for medicine and agricultural chemical.

EXAMPLES

The process for production of the compound of the present invention is described specifically by way of Examples. However, the present invention is in no way restricted by these Examples.

Example 1

Production of 4-(5-amino-3-trifluoromethyl-1H-1,2,4-triazol-1-yl)-3-fluorotoluene In a 50-ml eggplant flask provided with a magnetic stirrer were placed 3.08 g (20 mmol) of 2-fluoro-4-methylphenylboronic acid, 3.04 g (20 mmol) of 5-amino-3-trifluoromethyl-1H-1,2,4-triazol, 0.36 g (2 mmol) of copper (II) acetate, 2.58 g (2 mmol) of diisopropylethylamine and then 20 ml of acetonitrile. The mixture was stirred at room temperature for 3 days in a water bath. Thereto were added 30 ml of ethyl acetate, water and a saturated aqueous sodium bicarbonate solution to give rise to phase separation. The aqueous phase was extracted with 30 ml of ethyl acetate. The ethyl acetate phase was washed with 3% hydrochloric acid and then with a saturated aqueous sodium chloride solution. The ethyl acetate phase was dried over anhydrous sodium sulfate and subjected to vacuum distillation to distill off ethyl acetate. The residue was recrystallized from an ethyl acetate/n-hexane system to obtain a title compound as 2.45 g of a crystal. Yield: 47%
$^1$H NMR (300 MHz, CDCl$_3$) σ:
7.41 (dd, J=7.2 Hz, 1H), 7.13 (d, J=6.9, 1H),
7.12 (d, J=11.7 Hz, 1H), 4.83 (br, 2H),
2.45 (s, 3H) ppm
GC-MS: M$^+$=260

Example 2

Production of 4-(5-amino-3-trifluoromethyl-1H-1,2,4-triazol-1-yl)-1,3-dimethylbenzene In a 50-ml eggplant flask provided with a magnetic stirrer were placed 3.04 g (20 mmol) of 5-amino-3-trifluoromethyl-1H-1,2,4-triazole, 3.0 g (7.8 mmol) of 2,4-dimethylphenylboroxine, 127 mg (2 mmol) of a copper powder, 2.0 g (25 mmol) of pyridine and then 10 ml of N,N-dimethylformamide. The mixture was stirred at 60° C. for 24 hours. Thereto were added 30 ml of ethyl acetate, water and a saturated aqueous sodium bicarbonate solution to give rise to phase separation. The aqueous phase was extracted with 30 ml of ethyl acetate. The ethyl acetate phase was washed with 3% hydrochloric acid and then with a saturated aqueous sodium chloride solution. The ethyl acetate phase was dried over anhydrous sodium sulfate and subjected to vacuum distillation to distill off ethyl acetate. The residue was purified by silica gel column chromatography to obtain a title compound as 2.6 g of a crystal. Yield: 50%
$^1$H NMR (300 MHz, CDCl$_3$) σ:
7.22-7.13 (m, 3H), 4.79 (br, 2H), 2.40 (s, 3H),
2.15 (s, 3H) ppm
GC-MS: M$^+$=256

Example 3

Production of 1,3-dimethyl-4-(3-trifluoromethyl-1H-1,2,4-triazol-1-yl)benzene

In a 50-ml eggplant flask provided with a magnetic stirrer were placed 1.37 g (10 mmol) of 3-trifluoromethyl-1H-1,2,4-triazole, 1.32 g (3.33 mmol) of 2,4-dimethylphenylboroxine, 64 mg (1 mmol) of a copper powder, 0.8 g (10 mmol) of pyridine and then 5 ml of N,N-dimethylformamide. The mixture was stirred at 50° C. for 4 hours. Thereto were added 30 ml of ethyl acetate and 3% hydrochloric acid to give rise to phase separation. The aqueous phase was extracted with 30 mol of ethyl acetate. The ethyl acetate phase was washed with water and then with a saturated aqueous sodium chloride solution. The ethyl acetate phase was dried over anhydrous sodium sulfate and then subjected to vacuum distillation to distill off ethyl acetate to obtain a title compound as 2.3 g of a crystal. Yield: 95%
$^1$H NMR (300 MHz, CDCl$_3$) σ:
8.3 (s, 1H), 7.22-7.13 (m, 3H), 2.41 (s, 3H),
2.20 (s, 3H) ppm
GC-MS: M$^+$=241

Example 4

Production of 4-(5-amino-trifluoromethyl-1H-1,2,4-triazol-1-yl)-3-fluorobenzonitrile In a 50-ml eggplant flask provided with a magnetic stirrer were placed 3.04 g (20 mmol) of 5-amino-3-trifluoromethyl-1H-1,2,4-triazole, 3.06 g (22 mmol) of 3,4-difluorobenzonitrile, 2.76 g (20 mmol) of potassium carbonate and then 10 ml of N,N-dimethylformamide. The mixture was stirred at 60° C. for 6 hours. Thereto were added 50 ml of ethyl acetate and 50 ml of water to give rise to phase separation. The aqueous phase was extracted with 50 mol of ethyl acetate. The ethyl acetate phase was washed with water and then with a saturated aqueous sodium chloride solution. The ethyl acetate phase was dried over anhydrous sodium sulfate and then subjected to vacuum distillation to distill off ethyl acetate. To the residue was added 5 ml of toluene. The mixture was stirred with heating, cooled and then filtered to obtain 3.18 g of a crystal. Yield: 58.6%
GC-MS: M$^+$=271

Example 5

Production of 4-(5-amino-3-trifluoromethyl-1H-1,2,4-triazol-1-yl)-3-fluorotoluene In a 50-ml eggplant flask provided with a magnetic stirrer were placed 1.35 g (5 mmol) of 4-(5-amino-3-trifluoromethyl-1H-1,2,4-triazol-1-yl)-3-fluorobenzonitrile, 0.95 g (15 mmol) of ammonium formate and then 12 ml of methanol. Thereto was added 1.35 g of 10% palladium carbon in a nitrogen current. The mixture was stirred at room temperature for 24 hours. Gas chromatography detected, as components in the reaction mixture, 34% of 4-(5-amino-3-trifluoromethyl-1H-1,2,4-triazol-1-yl)-3-fluorotoluene and 55% of 4-(5-amino-3-trifluoromethyl-1H-1,2,4-triazol-1-yl)toluene.

Example 6

Production of 4-(5-amino-3-trifluoromethyl-1H-1,2,4-triazol-1-yl)-3-fluorotoluene 1) Production of N,N-diethyl-4-(5-amino-3-trifluoromethyl-1H-1,2,4-triazol-1-yl)-3-fluorobenzylamine In a 25-ml eggplant flask provided with a magnetic stirrer were placed 2.0 g of Raney nickel, 10 ml of deionized water and 0.5 g of a 25% aqueous sodium hydroxide solution. The mixture was stirred at 50° C. for 1 hour. Thereto was added 5.5 ml of a 48% aqueous sodium hydroxide solution. The mixture was stirred at 50° C. for 1 hour. The supernatant liquid was removed. The residue was washed seven times with 15 ml of deionized water by decantation. To the washed residue was added 15 ml of ethanol, followed by removal of the supernatant liquid. This operation was conducted four times. Thereby the solvent in the reaction system was substituted with ethanol sufficiently, followed by addition of 271 mg (1 mmol) of 4-(5-amino-3-trifluoromethyl-1H-1,2,4-triazol-1-yl)-3-fluorobenzonitrile. The mixture was refluxed with heating for 15 hours. The system was cooled to room temperature, followed by filtration. The filtrate was subjected to vacuum distillation to distill off the solvent, to obtain 0.37 g of oil. Gas chromatography confirmed that the purity of N,N-diethyl-4-(5-amino-3-trifluoromethyl-1H-1,2,4-triazol-1-yl)-3-fluorobenzylamine in the oil was 92%.

GC-MS: $M^+$=331

2) production of 4-(5-amino-3-trifluoromethyl-1H-1,2,4-triazol-1-yl)-3-fluorotoluene In a 25-ml eggplant flask provided with a magnetic stirrer were placed 0.37 g (1 mmol) of N,N-diethyl-4-(5-amino-3-trifluoromethyl-1H-1,2,4-triazol-1-yl)-3-fluorobenzylamine and then 2 ml of methanol. Thereto was added 75 mg of 5% palladium (II) hydroxide carbon in a nitrogen current. The mixture was stirred at room temperature for 72 hours in a hydrogen current, followed by filtration. To the filtrate were added 20 ml of ethyl acetate and 20 ml of water to give rise to phase separation. The aqueous phase was extracted with 20 ml of ethyl acetate. The ethyl acetate phase was washed with water and then with a saturated aqueous sodium chloride solution. The ethyl acetate phase was dried over anhydrous sodium sulfate and then subjected to vacuum distillation to distill off ethyl acetate, to obtain 0.22 g of a crystal. Gas chromatography detected, as components in the crystal, 69% of 4-(5-amino-3-trifluoromethyl-1H-1,2,4-triazol-1-yl)-3-fluorotoluene and 12% of 4-(5-amino-3-trifluoromethyl-1H-1,2,4-triazol-1-yl)toluene.

Example 7

Production of 5-(5-amino-3-trifluoromethyl-1H-1,2,4-triazol-1-yl)-4-fluoro-2-methylbenzenesulfonyl Chloride In a 25-ml eggplant flask provided with a magnetic stirrer were placed 2.91 g (25 mmol) of chlorosulfonic acid and then 1.3 g (5 mmol) of 4-(5-amino-3-trifluoromethyl-1H-1,2,4-triazol-1-yl)-3-fluorotoluene. The mixture was stirred at 80° C. for 3 hours and cooled to room temperature. The mixture was added onto ice in small portions, and 30 ml of ethyl acetate was added to give rise to phase separation. The aqueous phase was extracted with 30 ml of ethyl acetate. The ethyl acetate phase was washed with a saturated aqueous sodium chloride solution, dried over anhydrous sodium sulfate, and subjected to vacuum distillation to distill off ethyl acetate, to obtain a title compound as 1.66 g of a crystal. Yield: 93%

$^1$H NMR (300 MHz, CDCl$_3$) σ:

8.33 (d, J=7.2 Hz, 1H), 7.41 (d, J=10.5 Hz, 1H), 5.06 (br, 2H), 2.89 (s, 3H) ppm

GC-MS: $M^+$=358, $(M+2)^+$=360

Example 8

Production of 5-(5-amino-3-trifluoromethyl-1H-1,2,4-triazol-1-yl)-2,4-dimethylbenzenesulfonyl Chloride In a 25-ml eggplant flask provided with a magnetic stirrer were placed 5.83 g (50 mol) of chlorosulfonic acid and then 2.49 g (9.73 mmol) of 4-(5-amino-3-trifluoromethyl-1H-1,2,4-triazol-1-yl)-1,3-dimethylbenzene. The mixture was stirred at 60° C. for 2 hours. The mixture was cooled to room temperature and then added onto ice in small portions. Thereto was added 30 ml of ethyl acetate to give rise to phase separation. The aqueous phase was extracted with 30 ml of ethyl acetate. The ethyl acetate phase was washed with a saturated aqueous sodium chloride solution and then dried over anhydrous sodium sulfate. Then, vacuum distillation was conducted to distill off ethyl acetate to obtain a title compound as 3.3 g of a crystal. Yield: 96%

$^1$H NMR (300 MHz, CDCl$_3$) σ:

8.08 (s, 1H), 7.49 (s, 1H), 5.00 (br, 2H), 2.84 (s, 3H), 2.31 (s, 3H) ppm

GC-MS: $M^+$=354, $(M+2)^+$=356

Example 9

Production of 2,4-dimethyl-5-(3-trifluoromethyl-1H-1,2,4-triazol-1-yl)benzenesulfonyl Chloride In a 25-ml eggplant flask provided with a magnetic stirrer were placed 2.5 g (22 mol) of chlorosulfonic acid and then 1.8 g (7.4 mmol) of 1,3-dimethyl-4-(3-trifluoromethyl-1H-1,2,4-triazol-1-yl)benzene. The mixture was stirred at 70° C. for 2 hours. The mixture was cooled to room temperature and then added onto ice in small portions. Thereto was added 30 ml of ethyl acetate to give rise to phase separation. The aqueous phase was extracted with 30 ml of ethyl acetate. The ethyl acetate phase was washed with a saturated aqueous sodium chloride solution and then dried over anhydrous sodium sulfate. Then, vacuum distillation was conducted to distill off ethyl acetate to obtain a title compound as 2.5 g of brown oil. Yield: 99%

$^1$H NMR (300 MHz, CDCl$_3$) σ:

8.42 (s, 1H), 8.06 (s, 1H), 7.49 (s, 1H), 2.85 (s, 3H), 2.37 (s, 3H) ppm

GC-MS: $M^+$=339, $(M+2)^+$=341

Example 10

Production of 5-(5-amino-3-trifluoromethyl-1H-1,2,4-triazol-1-yl)-4-fluoro-2-methylthiophenol In a 25-ml eggplant flask provided with a magnetic stirrer was placed 1.83 g (5 mmol) of 5-(5-amino-3-trifluoromethyl-1H-1,2,4-triazol-1-yl)-4-fluoro-2-methylbenzenesulfonyl chloride, followed by addition of 1.6 g (25 mmol) of zinc, 10 ml of ethanol and 10 ml of (100 mmol) of 18% hydrochloric acid. The mixture was stirred at room temperature for 15 minutes. Then, the mixture was refluxed with heating until the zinc powder was dissolved completely. The mixture was cooled to room temperature. Thereto were added 30 ml of water and 30 ml of ethyl acetate to give rise to phase separation. The aqueous phase was extracted with 30 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain 1.5 g of a crystal. Yield: 100%

$^1$H NMR (300 MHz, CDCl$_3$) σ:
7.42 (d, J=7.2 Hz, 1H), 7.19 (d, J=10.5 Hz, 1H),
5.67 (br, 2H), 3.74 (br, 1H), 2.54 (s, 3H) ppm
LC-MS: M$^+$=292, (M−1)$^+$=291

Reference Example 1

Production of [5-(5-amino-3-trifluoromethyl-1H-1,2, 4-triazol-1-yl)-4-fluoro-2-methylphenyl]2,2,2-trifluoroethyl Sulfide In a 25-ml eggplant flask provided with a magnetic stirrer were placed 1.5 g (5 mmol) of 5-(5-amino-3-trifluoromethyl-1H-1,2,4-triazol-1-yl)-4-fluoro-2-methylthiophenol, 5 ml of N,N-dimethylformamide, 1.04 g (7.5 mmol) of potassium carbonate, 0.54 g (3.5 mmol) of Rongalit and 1.57 g (7.5 mmol) of 2,2,2-trifluoroethyl iodide. The mixture was stirred at room temperature for 16 hours. Thereto were added 30 ml of water and 30 ml of ethyl acetate to give rise to phase separation. The aqueous phase was extracted with 30 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain 1.4 g of a crystal. Yield: 74%. The $^1$H NMR spectrum of the crystal was confirmed to agree with the $^1$H NMR spectrum of the title compound produced by the process based on the Examples described in WO 2006/043635.

$^1$H NMR (300 MHz, CDCl$_3$) σ:
7.68 (d, J=7.2 Hz, 1H), 7.22 (d, J=10.5 Hz, 1H),
4.91 (br, 2H), 3.41 (q, J=9.6 Hz, 2H), 2.56 (s, 3H) ppm
GC-Ms: M$^+$=374

Reference Example 2

Production of [5-(5-amino-3-trifluoromethyl-1H-1,2, 4-triazol-1-yl)-4-fluoro-2-methylphenyl]2,2,2-trifluoroethyl Sulfoxide In a 25-ml eggplant flask provided with a magnetic stirrer were placed 0.06 g (0.16 mmol) of [5-(5-amino-3-trifluoromethyl-1H-1,2,4-triazol-1-yl)-4-fluoro-2-methylphenyl]2,2,2-trifluoroethyl sulfide, 0.5 ml of acetonitrile, 2.6 mg (0.008 mmol) of sodium tungstate dihydrate and 44 mg (0.39 mmol) of a 30% aqueous hydrogen peroxide solution. The mixture was stirred at room temperature for 16 hours. Thereto were added 10 ml of water and 10 ml of ethyl acetate to give rise to phase separation. The aqueous phase was extracted with 10 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain 0.05 g of a crystal. Yield: 80% The $^1$H NMR spectrum of the crystal was confirmed to agree with the $^1$H NMR spectrum of the title compound produced by the process based on the Examples described in WO 2006/043635.

$^1$H NMR (300 MHz, CDCl$_3$) σ:
8.20 (d, J=7.5 Hz, 1H), 7.29 (s, 1H), 4.86 (br, 2H), 3.52 (m, 2H), 2.50 (s, 3H) ppm
GC-Ms: M$^+$=390

Example 11

Production of 5-(5-amino-3-trifluoromethyl-1H-1,2, 4-triazol-1-yl)-2,4-dimethylthiophenol In a 25-ml eggplant flask provided with a magnetic stirrer was placed 3.3 g (9.3 mmol) of 5-(5-amino-3-trifluoromethyl-1H-1,2,4-triazol-1-yl)-2,4-dimethylbenzenesulfonyl chloride, followed by addition of 3.27 g (50 mmol) of zinc, 10 ml of ethanol and 5 ml (50 mmol) of 35% hydrochloric acid. The mixture was stirred at room temperature for 15 minutes. Then, the mixture was refluxed with heating, for 3 hours. The mixture was cooled to room temperature. Thereto were added 30 ml of water and 30 ml of ethyl acetate to give rise to phase separation. The aqueous phase was extracted with 30 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain a title compound as 1.9 g of oil. Yield: 71%

$^1$H NMR (300 MHz, CDCl$_3$) σ:
7.26 (s, 1H), 7.18 (s, 1H), 4.77 (br, 2H),
3.36 (br, 1H), 2.37 (s, 3H), 2.11 (s, 3H) ppm
GC-MS: M$^+$=288

Reference Example 3

Production of [5-(5-amino-3-trifluoromethyl-1H-1,2, 4-triazol-1-yl)-2,4-dimethylphenyl]2,2,2-trifluoroethyl Sulfide In a 25-ml eggplant flask provided with a magnetic stirrer were placed 1.85 g (6.4 mmol) of 5-(5-amino-3-trifluoromethyl-1H-1,2,4-triazol-1-yl)-2,4-dimethylthiophenol, 6 ml of N,N-dimethylformamide, 1.33 g (9.6 mmol) of potassium carbonate, 0.69 g (4.5 mmol) of Rongalit and 2.02 g (9.6 mmol) of 2,2,2-trifluoroethyl iodide. The mixture was stirred at room temperature for 24 hours. Thereto were added 50 ml of water and 50 ml of ethyl acetate to give rise to phase separation. The aqueous phase was extracted with 50 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain 1.87 g of a crystal. Yield: 79%. The $^1$H NMR spectrum of the crystal was confirmed to agree with the $^1$H NMR spectrum of the title compound produced by the process based on the Examples described in WO 2006/043635.

$^1$H NMR (300 MHz, CDCl$_3$) σ:
7.45 (s, 1H), 7.26 (s, 1H), 4.61 (br, 2H),
3.39 (q, J=9.6 Hz, 2H), 2.50 (s, 3H), 2.16 (s, 3H) ppm
GC-Ms: M$^+$=370

Example 12

Production of 2,4-dimethyl-5-(3-trifluoromethyl-1H-1,2,4-triazol-1-yl)thiophenol In a 50-ml eggplant flask provided with a magnetic stirrer was placed 3.44 g (9.6 mmol) of 2,4-dimethyl-5-(3-trifluoromethyl-1H-1,2,4-triazol-1-yl)benzenesulfonyl chloride, followed by addition of 3.14 g (48 mmol) of zinc, 16 ml of ethanol and 8 ml (80 mmol) of 35% hydrochloric acid. The mixture was stirred at room temperature for 30 minutes and then refluxed with heating, for 4 hours. The mixture was cooled to room temperature. Thereto were added 50 ml of water and 50 ml of ethyl acetate to give rise to phase separation. The aqueous phase was extracted with 50 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain a title compound as 2.25 g of a crystal. Yield: 86%

$^1$H NMR (300 MHz, CDCl$_3$) σ:
8.30 (s, 1H), 7.28 (s, 1H), 7.18 (s, 1H), 3.37 (br, 1H), 2.38 (s, 3H), 2.17 (s, 3H) ppm
GC-MS: M$^+$=273

Reference Example 4

Production of 2,2,2-trifluoroethyl[2,4-dimethyl-5-(3-trifluoromethyl-1H-1,2,4-triazol-1-yl)phenyl]sulfide In a 25-ml eggplant flask provided with a magnetic stirrer were placed 1.33 g (4.9 mmol) of 2,4-dimethyl-5-(3-trifluoromethyl-1H-1,2,4-triazol-1-yl)thiophenol, 5 ml of N,N-dimethylformamide, 1.01 g (7.3 mmol) of potassium carbonate, 0.53 g (3.4 mmol) of Rongalit and 1.53 g (7.3 mmol) of 2,2,2-trifluoroethyl iodide. The mixture was stirred at room temperature for 6 hours. Thereto were added 30 ml of water and 30 ml of ethyl acetate to give rise to phase separation. The aqueous phase was extracted with 30 ml of ethyl acetate. The ethyl acetate phase was washed with water and then with a saturated aqueous sodium chloride solution, and dried over anhydrous sodium sulfate. Vacuum distillation was conducted to distill off ethyl acetate to obtain 1.48 g of a crystal. Yield: 87%. The $^1$H NMR spectrum of the crystal was confirmed to agree with the $^1$H NMR spectrum of the title compound produced by the process based on the Examples described in WO 2006/043635.

$^1$H NMR (300 MHz, CDCl$_3$) σ:
8.31 (s, 1H), 7.46 (s, 1H), 7.26 (s, 1H),
3.39 (q, J=9.6 Hz, 2H), 2.52 (s, 3H), 2.21 (s, 3H) ppm
GC-Ms: M$^+$=355

Reference Example 5

Production of 2,2,2-trifluoroethyl[2,4-dimethyl-5-(3-trifluoromethyl-1H-1,2,4-triazol-1-yl)phenyl]sulfoxide In a 25-ml eggplant flask provided with a magnetic stirrer were placed 0.71 g (2 mmol) of 2,2,2-trifluoroethyl[2,4-dimethyl-5-(3-trifluoromethyl-1H-1,2,4-triazol-1-yl)phenyl] sulfide, 5 ml of acetonitrile, 17 mg (0.05 mmol) of sodium tungstate dihydrate and 0.25 g (2.2 mmol) of a 30% aqueous hydrogen peroxide solution. The mixture was stirred at room temperature for 24 hours. Thereto was added 0.25 g (2.2 mmol) of a 30% aqueous hydrogen peroxide solution, and the mixture was stirred at room temperature for 6 hours. Thereto were added 60 ml of water and 40 ml of ethyl acetate to give rise to phase separation. The aqueous phase was extracted with 40 ml of ethyl acetate. The ethyl acetate phase was washed with water and then with a saturated aqueous sodium chloride solution, and dried over anhydrous sodium sulfate. Vacuum distillation was conducted to distill off ethyl acetate. The residue was recrystallized from isopropanol to obtain 0.5 g of a crystal. Yield: 67% The $^1$H NMR spectrum of the crystal was confirmed to agree with the 1H NMR spectrum of the title compound produced by the process based on the Examples described in WO 2006/043635.

$^1$H NMR (300 MHz, CDCl$_3$) σ:
8.39 (s, 1H), 7.96 (s, 1H), 7.33 (s, 1H),
3.47 (dq, J=9.9, 3.3 Hz, 2H), 2.45 (s, 3H),
2.32 (s, 3H) ppm
GC-Ms: M$^+$=371

The invention claimed is:

1. An aryl (1H-1,2,4-triazol-1-yl) compound represented by the general formula (1):

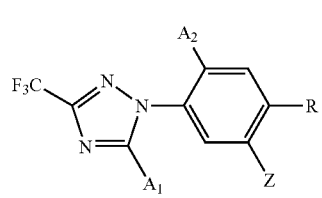

(1)

wherein R is a methyl group; $A_1$ is $NH_2$; $A_2$ is a fluorine atom; and Z is a hydrogen atom or a chlorosulfonyl group.

2. An aryl (1H-1,2,4-triazol-1-yl) compound as claimed in claim 1, wherein Z is a hydrogen atom.

3. An aryl (1H-1,2,4-triazol-1-yl) compound as claimed in claim 1, wherein Z is a chlorosulfonyl group.

* * * * *